(12) United States Patent
Fallin et al.

(10) Patent No.: US 10,492,838 B2
(45) Date of Patent: Dec. 3, 2019

(54) FLEXIBLE BONE IMPLANT

(71) Applicant: IntraFuse, LLC, Logan, UT (US)

(72) Inventors: T. Wade Fallin, Hyde Park, UT (US); M. Mary Sinnott, Logan, UT (US); Robert W. Hoy, Essex Junction, VT (US)

(73) Assignee: IntraFuse, LLC, Logan, UT (US)

( * ) Notice: Subject to any disclaimer, the term of this patent is extended or adjusted under 35 U.S.C. 154(b) by 0 days.

(21) Appl. No.: 15/354,571

(22) Filed: Nov. 17, 2016

(65) Prior Publication Data

US 2017/0079698 A1    Mar. 23, 2017

Related U.S. Application Data

(63) Continuation-in-part of application No. 15/285,608, filed on Oct. 5, 2016, which is a continuation-in-part of application No. 15/197,879, filed on Jun. 30, 2016.

(60) Provisional application No. 62/191,904, filed on Jul. 13, 2015, provisional application No. 62/238,780, filed on Oct. 8, 2015.

(51) Int. Cl.
*A61B 17/72* (2006.01)
*A61B 17/00* (2006.01)

(52) U.S. Cl.
CPC ...... *A61B 17/7208* (2013.01); *A61B 17/7225* (2013.01); *A61B 17/7291* (2013.01); *A61B 17/7216* (2013.01); *A61B 2017/00004* (2013.01)

(58) Field of Classification Search
CPC ... A61B 17/86; A61B 17/164; A61B 17/1642; A61B 17/1655; A61B 17/869; A61B 17/863; A61B 17/8635; A61B 17/7208; A61B 17/7291
See application file for complete search history.

(56) References Cited

U.S. PATENT DOCUMENTS

| | | | |
|---|---|---|---|
| 2,267,925 A | 12/1941 | Johnston | |
| 2,801,631 A * | 8/1957 | Charnley | A61B 17/746 606/65 |
| 3,103,926 A * | 9/1963 | Cochran | A61B 17/72 606/104 |
| 3,118,444 A | 1/1964 | Serrato, Jr. | |
| 3,456,272 A | 7/1969 | Wendt | |
| 3,680,553 A | 8/1972 | Seppo | |
| 3,717,146 A | 2/1973 | Halloran | |

(Continued)

FOREIGN PATENT DOCUMENTS

DE    202008016697 U1    3/2009
WO    WO2006124764 A1    11/2006
(Continued)

OTHER PUBLICATIONS

International Search Report and Written Opinion for International Application No. PCT/US2016/041162 dated Oct. 12, 2016, 18 pp.
(Continued)

*Primary Examiner* — David W Bates
(74) *Attorney, Agent, or Firm* — David Meibos; Maywood IP Law

(57) ABSTRACT

Examples of devices and methods for stabilizing a fracture in a bone include a body having an elongate distal portion having an outer surface defining a screw thread and an elongate proximal portion having a non-threaded outer surface.

21 Claims, 20 Drawing Sheets

(56) References Cited

U.S. PATENT DOCUMENTS

| | | |
|---|---|---|
| 3,760,802 A | 9/1973 | Fischer |
| 3,763,855 A | 10/1973 | McAtee |
| 3,779,239 A | 12/1973 | Fischer |
| 3,805,775 A | 4/1974 | Fischer |
| 4,016,874 A | 4/1977 | Maffei |
| 4,059,102 A * | 11/1977 | Devas ............... A61B 17/863 606/309 |
| 4,170,990 A | 10/1979 | Baumgart |
| 4,175,555 A * | 11/1979 | Herbert ............. A61B 17/863 606/304 |
| 4,212,294 A | 7/1980 | Murphy |
| 4,262,665 A | 4/1981 | Roalstad |
| 4,328,839 A | 5/1982 | Lyons |
| 4,453,539 A | 6/1984 | Raftopoulos |
| 4,457,301 A | 7/1984 | Walker |
| 4,463,753 A | 8/1984 | Gustilo |
| 4,475,545 A | 10/1984 | Ender |
| 4,483,335 A | 11/1984 | Tornier |
| 4,492,226 A | 1/1985 | Belykh |
| 4,590,930 A | 5/1986 | Kurth |
| 4,697,585 A | 10/1987 | Williams |
| 4,706,659 A | 11/1987 | Matthews |
| 4,751,922 A | 6/1988 | DiPietropolo |
| 4,858,602 A | 8/1989 | Seidel |
| 4,947,502 A | 8/1990 | Engelhardt |
| 4,959,064 A | 9/1990 | Engelhardt |
| 5,017,057 A | 5/1991 | Kryger |
| 5,019,079 A * | 5/1991 | Ross ................. A61B 17/863 411/389 |
| 5,032,133 A | 7/1991 | Carbone |
| 5,053,035 A | 10/1991 | McLaren |
| 5,061,137 A | 10/1991 | Gourd |
| 5,116,336 A | 5/1992 | Frigg |
| 5,116,378 A | 5/1992 | Carbone |
| 5,259,398 A * | 11/1993 | Vrespa ............... A61B 17/863 128/898 |
| 5,281,225 A | 1/1994 | Vicenzi |
| 5,312,255 A * | 5/1994 | Bauer ................. A61C 8/0012 433/173 |
| 5,334,184 A | 8/1994 | Bimman |
| 5,356,127 A | 10/1994 | Moore |
| 5,374,235 A | 12/1994 | Ahrens |
| 5,397,328 A | 3/1995 | Behrens |
| 5,409,490 A | 4/1995 | Ethridge |
| 5,415,660 A | 5/1995 | Campbell |
| 5,437,674 A | 8/1995 | Worcel |
| 5,456,267 A * | 10/1995 | Stark ................. A61B 10/025 128/898 |
| 5,480,400 A | 1/1996 | Berger |
| 5,527,316 A | 6/1996 | Stone |
| 5,536,127 A * | 7/1996 | Pennig ............... A61B 17/863 411/397 |
| 5,575,790 A | 11/1996 | Chen |
| 5,603,715 A | 2/1997 | Kessler |
| 5,609,595 A * | 3/1997 | Pennig ............... A61B 17/80 606/104 |
| 5,676,667 A * | 10/1997 | Hausman ............ A61B 17/80 606/281 |
| 5,681,289 A | 10/1997 | Wilcox |
| 5,709,687 A | 1/1998 | Pennig |
| 5,827,289 A | 10/1998 | Reiley |
| 5,871,486 A | 2/1999 | Huebner |
| 5,891,101 A | 4/1999 | Wilcox |
| 5,895,375 A | 4/1999 | Wilcox |
| 5,972,015 A | 10/1999 | Scribner |
| 5,993,450 A | 11/1999 | Worcel |
| 6,019,762 A * | 2/2000 | Cole ................. A61B 17/8047 606/104 |
| 6,030,162 A | 2/2000 | Huebner |
| 6,053,922 A | 4/2000 | Krause |
| 6,162,234 A | 12/2000 | Freedland |
| 6,197,031 B1 | 3/2001 | Barrette |
| 6,224,600 B1 | 5/2001 | Protogirou |
| 6,248,110 B1 | 6/2001 | Reiley |
| 6,280,456 B1 | 8/2001 | Scribner |
| 6,299,615 B1 | 10/2001 | Huebner |
| 6,319,255 B1 | 11/2001 | Grundei |
| 6,322,562 B1 | 11/2001 | Wolter |
| 6,338,732 B1 * | 1/2002 | Yang ................. A61B 17/7216 606/311 |
| 6,368,326 B1 | 4/2002 | Dakin |
| 6,416,517 B2 | 7/2002 | Harder |
| 6,447,514 B1 | 9/2002 | Stalcup |
| 6,447,515 B1 | 9/2002 | Meldrum |
| 6,447,518 B1 | 9/2002 | Krause |
| 6,517,541 B1 | 2/2003 | Sesic |
| 6,524,313 B1 | 2/2003 | Fassier |
| 6,551,321 B1 | 4/2003 | Burkinshaw |
| 6,554,833 B2 | 4/2003 | Levy |
| 6,605,090 B1 | 8/2003 | Trieu |
| 6,613,052 B1 | 9/2003 | Kinnett |
| 6,623,505 B2 | 9/2003 | Scribner |
| 6,632,235 B2 | 10/2003 | Weikel |
| 6,656,184 B1 | 12/2003 | White |
| 6,736,819 B2 | 5/2004 | Tipirneni |
| 6,749,611 B2 | 6/2004 | Venturini |
| 6,790,210 B1 | 9/2004 | Cragg |
| 6,852,115 B2 | 2/2005 | Kinnett |
| 6,875,215 B2 | 4/2005 | Taras |
| 6,899,719 B2 | 5/2005 | Reiley |
| 6,921,403 B2 * | 7/2005 | Cragg ................. A61B 17/1671 606/246 |
| 6,949,100 B1 | 9/2005 | Venturini |
| 6,949,101 B2 | 9/2005 | McCleary |
| 6,955,513 B2 | 10/2005 | Niku |
| 7,041,106 B1 | 5/2006 | Carver |
| 7,044,954 B2 | 5/2006 | Reiley |
| 7,070,601 B2 * | 7/2006 | Culbert ............... A61B 17/685 606/311 |
| 7,156,861 B2 | 1/2007 | Scribner |
| 7,175,626 B2 | 2/2007 | Neff |
| 7,249,923 B2 | 7/2007 | Niku |
| 7,255,712 B1 | 8/2007 | Steinberg |
| 7,527,611 B2 | 5/2009 | Sweeney |
| 7,527,627 B2 | 5/2009 | Ferrante |
| 7,534,244 B2 | 5/2009 | Ferrante |
| 7,534,245 B2 | 5/2009 | Chappuis |
| 7,588,577 B2 | 9/2009 | Fencl |
| 7,591,823 B2 | 9/2009 | Tipirneni |
| 7,621,912 B2 | 11/2009 | Harms |
| 7,625,395 B2 | 12/2009 | Mückter |
| 7,632,277 B2 | 12/2009 | Woll |
| 7,666,205 B2 | 2/2010 | Weikel |
| 7,682,364 B2 | 3/2010 | Reiley |
| 7,708,766 B2 * | 5/2010 | Anderson .......... A61B 17/7071 606/105 |
| 7,722,611 B2 | 5/2010 | Cavallazzi |
| 7,727,263 B2 | 6/2010 | Cragg |
| 7,744,599 B2 | 6/2010 | Cragg |
| 7,766,968 B2 | 8/2010 | Sweeney |
| 7,776,042 B2 * | 8/2010 | Ainsworth ........... A61B 17/70 606/249 |
| 7,780,667 B2 | 8/2010 | Watanabe |
| 7,799,053 B2 | 9/2010 | Haid, Jr. |
| 7,819,874 B2 | 10/2010 | Woll |
| 7,842,095 B2 | 11/2010 | Klein |
| 7,846,162 B2 | 12/2010 | Nelson |
| 7,883,509 B2 | 2/2011 | Ferrante |
| 7,901,412 B2 | 3/2011 | Tipirneni |
| 7,909,825 B2 | 3/2011 | Saravia |
| 7,914,533 B2 | 3/2011 | Nelson |
| 7,918,853 B2 | 4/2011 | Watanabe |
| 7,931,652 B2 | 4/2011 | Ferrante |
| 7,942,875 B2 | 5/2011 | Nelson |
| 8,007,498 B2 | 8/2011 | Mische |
| 8,012,155 B2 | 9/2011 | Prygoski |
| 8,034,071 B2 | 10/2011 | Scribner |
| 8,062,270 B2 | 11/2011 | Sweeney |
| 8,066,748 B2 | 11/2011 | Lieberman |
| 8,083,742 B2 | 12/2011 | Martin |
| 8,105,326 B2 | 1/2012 | Ferrante |
| 8,109,936 B2 | 2/2012 | Tipirneni |
| 8,128,626 B2 | 3/2012 | Justin |

(56) References Cited

U.S. PATENT DOCUMENTS

| | | |
|---|---|---|
| 8,128,627 B2 | 3/2012 | Justin |
| 8,147,492 B2 | 4/2012 | Justin |
| 8,162,943 B2 | 4/2012 | Justin |
| 8,167,881 B2 | 5/2012 | Justin |
| 8,187,275 B2 | 5/2012 | Ferrante |
| 8,197,523 B2 | 6/2012 | Bottlang |
| 8,206,389 B2 | 6/2012 | Huebner |
| 8,221,419 B2 | 7/2012 | Frigg |
| 8,246,691 B2 | 8/2012 | Mangiardi |
| 8,287,538 B2 | 10/2012 | Brenzel |
| 8,287,539 B2 | 10/2012 | Nelson |
| 8,287,541 B2 | 10/2012 | Nelson |
| 8,298,234 B2 | 10/2012 | Ferrante |
| 8,303,589 B2 | 11/2012 | Tyber |
| 8,313,488 B2 | 11/2012 | Schlienger |
| 8,317,789 B2 | 11/2012 | LeCronier |
| 8,317,846 B2 | 11/2012 | Bottlang |
| 8,328,806 B2 | 12/2012 | Tyber |
| 8,343,197 B2 * | 1/2013 | Gonzalez-Hernandez ................. A61B 17/1728 606/286 |
| 8,343,199 B2 | 1/2013 | Tyber |
| 8,382,760 B2 | 2/2013 | Mantovani |
| 8,388,620 B2 | 3/2013 | Brunnarius |
| 8,398,690 B2 | 3/2013 | Bottlang |
| 8,403,938 B2 | 3/2013 | Aeschlimann |
| 8,409,208 B2 * | 4/2013 | Abdou ............... A61B 17/7055 606/86 R |
| 8,430,879 B2 | 4/2013 | Stoneburner |
| 8,435,238 B2 | 5/2013 | Dejardin |
| 8,435,272 B2 | 5/2013 | Dougherty |
| 8,439,916 B2 | 5/2013 | Coati |
| 8,439,917 B2 | 5/2013 | Saravia |
| 8,449,574 B2 | 5/2013 | Biedermann |
| 8,460,293 B2 | 6/2013 | Coati |
| 8,496,657 B2 | 7/2013 | Bonutti |
| 8,496,658 B2 | 7/2013 | Stoneburner |
| 8,496,712 B2 | 7/2013 | Reiley |
| 8,507,614 B2 | 8/2013 | Shalaby |
| 8,529,611 B2 | 9/2013 | Champagne |
| 8,545,499 B2 | 10/2013 | Lozier |
| 8,568,413 B2 | 10/2013 | Mazur |
| 8,597,337 B2 | 12/2013 | Champagne |
| 8,608,743 B2 | 12/2013 | Baumgartner |
| 8,617,161 B2 | 12/2013 | Ferrante |
| 8,617,585 B2 | 12/2013 | Boden |
| 8,622,739 B2 | 1/2014 | Karmon |
| 8,632,543 B2 | 1/2014 | Metzinger |
| 8,632,570 B2 | 1/2014 | Biedermann |
| 8,652,141 B2 | 2/2014 | Rush |
| 8,663,224 B2 | 3/2014 | Overes |
| 8,663,326 B2 | 3/2014 | Osman |
| 8,679,120 B2 | 3/2014 | Frigg |
| 8,679,167 B2 | 3/2014 | Tipirneni |
| 8,696,719 B2 | 4/2014 | Lofthouse |
| 8,702,768 B2 | 4/2014 | Tipirneni |
| 8,709,055 B2 | 4/2014 | Beyar |
| 8,721,690 B2 | 5/2014 | Harms |
| 8,734,497 B2 | 5/2014 | Goel |
| 8,740,955 B2 | 6/2014 | Bottlang |
| 8,784,491 B2 | 7/2014 | Biedermann |
| 8,801,722 B2 | 8/2014 | Aeschlimann |
| 8,808,337 B2 | 8/2014 | Sweeney |
| 8,808,338 B2 | 8/2014 | Martin |
| 8,821,494 B2 | 9/2014 | Pilgeram |
| 8,828,067 B2 | 9/2014 | Tipirneni |
| 8,834,468 B2 | 9/2014 | Justin |
| 8,840,612 B2 | 9/2014 | Tontz |
| 8,870,836 B2 | 10/2014 | Sweeney |
| 8,888,815 B2 | 11/2014 | Holmes, Jr. |
| 8,900,233 B2 | 12/2014 | Logan |
| 8,939,978 B2 | 1/2015 | Watanabe |
| 8,961,516 B2 | 2/2015 | Nelson |
| 8,979,930 B2 * | 3/2015 | Glazer ................. A61F 2/442 623/17.11 |
| 8,992,615 B2 | 3/2015 | Pitkin |
| 8,998,999 B2 | 4/2015 | Lewis |
| 9,033,984 B2 | 5/2015 | Overes |
| 9,060,820 B2 | 6/2015 | Nelson |
| 9,072,510 B2 | 7/2015 | Thornes |
| 9,078,716 B2 * | 7/2015 | Pech .................. A61B 17/7225 |
| 9,259,250 B2 * | 2/2016 | Saravia ............. A61B 17/1725 |
| 9,314,286 B2 | 4/2016 | Bottlang |
| 9,421,045 B2 | 8/2016 | Justin |
| 9,480,515 B2 * | 11/2016 | Champagne ......... A61B 17/863 |
| 9,482,260 B1 * | 11/2016 | Krause .................. F16B 35/041 |
| 9,498,264 B2 | 11/2016 | Harshman et al. |
| 9,522,019 B2 | 12/2016 | Biedermann |
| 9,877,760 B2 * | 1/2018 | Ehler .................. A61B 17/846 |
| 2002/0143335 A1 * | 10/2002 | von Hoffmann ...... A61B 17/68 606/67 |
| 2002/0198527 A1 | 12/2002 | Muckter |
| 2003/0187447 A1 | 10/2003 | Ferrante |
| 2003/0229372 A1 | 12/2003 | Reiley |
| 2004/0049192 A1 | 3/2004 | Shimizu |
| 2004/0122455 A1 | 6/2004 | Lin |
| 2004/0127898 A1 | 7/2004 | Adam |
| 2004/0167519 A1 | 8/2004 | Weiner |
| 2005/0055024 A1 | 3/2005 | James |
| 2005/0119662 A1 | 6/2005 | Reiley |
| 2005/0131267 A1 | 6/2005 | Talmadge |
| 2005/0131268 A1 | 6/2005 | Talmadge |
| 2005/0165402 A1 | 7/2005 | Taras |
| 2005/0165405 A1 | 7/2005 | Tsou |
| 2005/0182402 A1 | 8/2005 | Hansson |
| 2005/0209629 A1 | 9/2005 | Kerr |
| 2006/0015123 A1 | 1/2006 | Fencl et al. |
| 2006/0030852 A1 | 2/2006 | Sevrain |
| 2006/0149265 A1 | 7/2006 | James |
| 2006/0155281 A1 | 7/2006 | Kaup |
| 2006/0173291 A1 | 8/2006 | Glossop |
| 2006/0235460 A1 | 10/2006 | Reiley |
| 2006/0271061 A1 | 11/2006 | Beyar |
| 2006/0293667 A1 | 12/2006 | Vignery |
| 2007/0005146 A1 | 1/2007 | Heyligers |
| 2007/0016190 A1 | 1/2007 | Martinez |
| 2007/0016204 A1 | 1/2007 | Martinez |
| 2007/0060941 A1 | 3/2007 | Reiley |
| 2007/0083207 A1 | 4/2007 | Ziolo |
| 2007/0276382 A1 | 11/2007 | Mikhail |
| 2008/0004626 A1 | 1/2008 | Glazer |
| 2008/0039941 A1 | 2/2008 | Steinberg |
| 2008/0051825 A1 | 2/2008 | Reiley |
| 2008/0058823 A1 | 3/2008 | Reiley |
| 2008/0058824 A1 | 3/2008 | Reiley |
| 2008/0058828 A1 | 3/2008 | Reiley |
| 2008/0109008 A1 | 5/2008 | Schwager |
| 2008/0125805 A1 | 5/2008 | Mische |
| 2008/0132896 A1 | 6/2008 | Bowen |
| 2008/0140078 A1 | 6/2008 | Nelson |
| 2008/0149115 A1 | 6/2008 | Hauck |
| 2008/0188895 A1 | 8/2008 | Cragg |
| 2008/0221620 A1 | 9/2008 | Krause |
| 2008/0234752 A1 | 9/2008 | Dahners |
| 2008/0249574 A1 | 10/2008 | Krause et al. |
| 2008/0249580 A1 | 10/2008 | Evans |
| 2008/0255555 A1 | 10/2008 | Justis |
| 2008/0269759 A1 | 10/2008 | Reiley |
| 2008/0269795 A1 | 10/2008 | Reiley |
| 2008/0269796 A1 | 10/2008 | Reiley |
| 2009/0005782 A1 | 1/2009 | Chirico |
| 2009/0005821 A1 | 1/2009 | Chirico |
| 2009/0012564 A1 | 1/2009 | Chirico |
| 2009/0018542 A1 | 1/2009 | Saravia |
| 2009/0062868 A1 | 3/2009 | Casutt |
| 2009/0062928 A1 | 3/2009 | Pitkin |
| 2009/0076517 A1 | 3/2009 | Reiley |
| 2009/0131991 A1 | 5/2009 | Tipirneni |
| 2009/0143781 A1 | 6/2009 | Mische |
| 2009/0149890 A1 * | 6/2009 | Martin ............... A61B 17/1717 606/316 |
| 2009/0157078 A1 | 6/2009 | Mikol |
| 2009/0264937 A1 | 10/2009 | Parrott |
| 2010/0016905 A1 | 1/2010 | Greenhalgh |

(56) References Cited

U.S. PATENT DOCUMENTS

| | | | |
|---|---|---|---|
| 2010/0023057 A1 | 1/2010 | Aeschlimann | |
| 2010/0069970 A1 | 3/2010 | Lewis | |
| 2010/0076503 A1 | 3/2010 | Beyar | |
| 2010/0082036 A1 | 4/2010 | Reiley | |
| 2010/0114097 A1 | 5/2010 | Siravo | |
| 2010/0114181 A1 | 5/2010 | Lob | |
| 2010/0121326 A1 | 5/2010 | Woll | |
| 2010/0137862 A1 | 6/2010 | Diao | |
| 2010/0145396 A1 | 6/2010 | Thornes | |
| 2010/0168755 A1 | 7/2010 | Reiley | |
| 2010/0179551 A1 | 7/2010 | Keller | |
| 2010/0211076 A1 | 8/2010 | Germain | |
| 2010/0228301 A1 | 9/2010 | Greenhalgh | |
| 2010/0256731 A1 | 10/2010 | Mangiardi | |
| 2010/0274246 A1 | 10/2010 | Beyar | |
| 2010/0286692 A1 | 11/2010 | Greenhalgh | |
| 2010/0292695 A1* | 11/2010 | May | A61B 17/1642 606/64 |
| 2010/0312292 A1 | 12/2010 | Tipirneni | |
| 2010/0318087 A1 | 12/2010 | Scribner | |
| 2011/0009865 A1 | 1/2011 | Orfaly | |
| 2011/0009907 A1 | 1/2011 | Klein | |
| 2011/0118740 A1 | 5/2011 | Rabiner | |
| 2011/0144703 A1* | 6/2011 | Krause | A61B 17/8625 606/309 |
| 2011/0160728 A1* | 6/2011 | Blitz | A61B 17/1725 606/64 |
| 2011/0172667 A1 | 7/2011 | Richards | |
| 2011/0178520 A1 | 7/2011 | Taylor | |
| 2011/0184472 A1 | 7/2011 | Niederberger | |
| 2011/0196371 A1 | 8/2011 | Forsell | |
| 2011/0196435 A1 | 8/2011 | Forsell | |
| 2011/0218585 A1 | 9/2011 | Krinke | |
| 2011/0282346 A1 | 11/2011 | Pham | |
| 2011/0282398 A1 | 11/2011 | Overes | |
| 2011/0295255 A1 | 12/2011 | Roberts | |
| 2011/0306975 A1 | 12/2011 | Kaikkonen | |
| 2012/0029432 A1 | 2/2012 | Sweeney | |
| 2012/0029579 A1 | 2/2012 | Bottlang | |
| 2012/0065638 A1 | 3/2012 | Moore | |
| 2012/0065692 A1 | 3/2012 | Champagne | |
| 2012/0123481 A1 | 5/2012 | Lin | |
| 2012/0172936 A1 | 7/2012 | Horrell | |
| 2012/0203346 A1 | 8/2012 | Kraus | |
| 2012/0209267 A1 | 8/2012 | Lee | |
| 2012/0221009 A1 | 8/2012 | Tada | |
| 2012/0226362 A1 | 9/2012 | Mische | |
| 2012/0232533 A1 | 9/2012 | Veldman | |
| 2012/0232597 A1 | 9/2012 | Saidha | |
| 2012/0239037 A1 | 9/2012 | Justin | |
| 2012/0239038 A1 | 9/2012 | Saravia | |
| 2012/0289961 A1 | 11/2012 | Frigg | |
| 2013/0035689 A1 | 2/2013 | Nanavati | |
| 2013/0041412 A1 | 2/2013 | Moumene | |
| 2013/0079829 A1 | 3/2013 | Globerman | |
| 2013/0123857 A1 | 5/2013 | Biedermann | |
| 2013/0131678 A1 | 5/2013 | Dahners | |
| 2013/0184765 A1 | 7/2013 | Beyar | |
| 2013/0190762 A1 | 7/2013 | Frankle | |
| 2013/0218214 A1 | 8/2013 | Beyar | |
| 2013/0226180 A1 | 8/2013 | Lee | |
| 2013/0231665 A1 | 9/2013 | Saravia | |
| 2013/0231666 A1 | 9/2013 | Lee | |
| 2013/0237813 A1 | 9/2013 | Beyar | |
| 2013/0267953 A1 | 10/2013 | Brenzel | |
| 2013/0296863 A1 | 11/2013 | Globerman | |
| 2013/0296952 A1 | 11/2013 | Globerman | |
| 2013/0297035 A1 | 11/2013 | Reiley | |
| 2013/0317556 A1 | 11/2013 | Goldzak | |
| 2013/0325007 A1 | 12/2013 | Beyar | |
| 2013/0325077 A1 | 12/2013 | Champagne | |
| 2013/0340240 A1 | 12/2013 | Irawan | |
| 2014/0031823 A1 | 1/2014 | Mazur | |
| 2014/0039495 A1 | 2/2014 | Bonutti | |
| 2014/0058390 A1 | 2/2014 | Taylor | |
| 2014/0058391 A1 | 2/2014 | Appenzeller | |
| 2014/0058432 A1 | 2/2014 | Scribner | |
| 2014/0074252 A1 | 3/2014 | Baumgartner | |
| 2014/0106306 A1 | 4/2014 | Karmon | |
| 2014/0114312 A1 | 4/2014 | Krause | |
| 2014/0128870 A1 | 5/2014 | Brenzel | |
| 2014/0131909 A1 | 5/2014 | Osman | |
| 2014/0163557 A1 | 6/2014 | Beyar | |
| 2014/0163624 A1 | 6/2014 | Siegal | |
| 2014/0180428 A1 | 6/2014 | McCormick | |
| 2014/0188113 A1 | 7/2014 | Overes | |
| 2014/0194877 A1 | 7/2014 | Mangiardi | |
| 2014/0207138 A1 | 7/2014 | Justin | |
| 2014/0222001 A1 | 8/2014 | Beyar | |
| 2014/0222080 A1 | 8/2014 | Biedermann | |
| 2014/0222091 A1 | 8/2014 | Champagne | |
| 2014/0249529 A1 | 9/2014 | LeCronier | |
| 2014/0288651 A1 | 9/2014 | Biedermann | |
| 2014/0316469 A1 | 10/2014 | Harms | |
| 2014/0336653 A1 | 11/2014 | Bromer | |
| 2014/0336663 A1 | 11/2014 | Mayer | |
| 2014/0358146 A1 | 12/2014 | Meek | |
| 2014/0371747 A1 | 12/2014 | Martin | |
| 2015/0005827 A1 | 1/2015 | Lin | |
| 2015/0012048 A1* | 1/2015 | Huebner | A61B 17/864 606/304 |
| 2015/0039033 A1 | 2/2015 | McCombs et al. | |
| 2015/0045791 A1 | 2/2015 | Mangiardi | |
| 2015/0045792 A1 | 2/2015 | Mangiardi | |
| 2015/0066097 A1 | 3/2015 | Biedermann | |
| 2015/0105830 A1 | 4/2015 | Biedermann | |
| 2015/0133937 A1 | 5/2015 | Benedict | |
| 2015/0157371 A1 | 6/2015 | Ehmke et al. | |
| 2015/0190186 A1* | 7/2015 | Fang | A61B 17/864 606/304 |
| 2015/0250503 A1 | 9/2015 | Tipirneni | |
| 2015/0374411 A1* | 12/2015 | Ehmke | A61B 17/686 606/329 |
| 2016/0128742 A9 | 5/2016 | Justin | |
| 2016/0317201 A1 | 11/2016 | Justin | |
| 2017/0119446 A1* | 5/2017 | Suh | A61B 17/88 |

FOREIGN PATENT DOCUMENTS

| | | |
|---|---|---|
| WO | WO2008064346 A2 | 5/2008 |
| WO | WO2008064347 A2 | 5/2008 |
| WO | WO2008064350 A2 | 5/2008 |
| WO | WO2009009772 A1 | 1/2009 |
| WO | WO2009076086 A1 | 6/2009 |
| WO | WO2009152270 A1 | 12/2009 |
| WO | WO2009152272 A1 | 12/2009 |
| WO | WO2009152273 A1 | 12/2009 |
| WO | WO2010037038 A2 | 4/2010 |
| WO | WO2010062379 A1 | 6/2010 |
| WO | WO2010099239 A3 | 1/2011 |
| WO | WO2011116078 A1 | 9/2011 |
| WO | WO2011154891 A2 | 12/2011 |
| WO | WO2012051137 A1 | 4/2012 |
| WO | WO2012069727 A1 | 5/2012 |
| WO | WO2012089330 A1 | 7/2012 |
| WO | WO2012089331 A1 | 7/2012 |
| WO | WO2012091681 A3 | 8/2012 |
| WO | WO2012107913 A2 | 8/2012 |
| WO | WO2012156915 A2 | 11/2012 |
| WO | WO2013063145 A1 | 5/2013 |
| WO | WO2013074884 A1 | 5/2013 |
| WO | WO2013166328 A1 | 11/2013 |
| WO | WO2014031947 A1 | 2/2014 |
| WO | WO2014031951 A1 | 2/2014 |
| WO | WO2014060576 A1 | 4/2014 |
| WO | WO2014060578 A1 | 4/2014 |
| WO | WO2014151907 A2 | 9/2014 |
| WO | WO2015029042 A1 | 3/2015 |

OTHER PUBLICATIONS

EPIFISA Centromedullary Nail, FH Orthopedics, www.f-h-fr, May 2005, 2 pp.

(56) References Cited

OTHER PUBLICATIONS

Dual-Trak Clavicle Screw Surgical Technique, Acumed, www.acumed.net, Sep. 2014, 12 pp.
Fibual Rod System Surgical Technique, Acumed, www.acumed.net, Apr. 2014, 8 pp.
Polarus Plus Humeral Rod, Acumed, www.acumed.net, Nov. 2008, 12 pp.
Asloum, Y., et al., "Internal Fixation of the Fibula in Ankle Fractures. A Prospective, Randomized and Comparative Study: Plating Versus Nailing", Orthopaedics & Traumatology: Surgery & Research 100(2014) S255-S259.
Rockwood Clavicle Pin, Design Rationale and Surgical Technique, Biomet Orthopedics, www.biomet.com, Aug. 31, 2012, 24 pp.
Distal Radius 3D Fracture Management System Surgical Technique, Conventus Orthopaedics, www.conventusortho.com, 12 pp.
Clavicle Fracture Repair Device, Sonoma Orthopedic Products, Inc., www.sonomaorthopedics.com, 2011, 6 pp.
The Nancy Nail Surgical Technique, DePuy Products, www.jnjgateway.com, 1999, 6 pp.
Hand Innovations Minimally Invasive Dorsal Endoplate Surgical Technique, Hand Innovations, www.handinnovations.com, 14 pp.
Latif, Girgis, et al., "The Effect of Percutaneous Screw Fixation of Lateral Malleolus on Ankle Fracture Healing and Function", Surgical Science, 2013, 4, 365-370, 2013.
Ankle Fracture System Abbreviated Surgical Technique, Sonoma Orthopedic Products, Inc., www.sonomaorthopedics.com, 2015, 20 pp.
Fracture and Fixation Products, ConMed Linvatec,, 7 pp.
Flexible Radial Nail Enclouage Radial Souple, www.evolutisfrance.com, 4 pp.
Olecranon Threaded Compression Rod: O'Rod, Acumed, www.acumed.net, Jul. 2010, 8 pp.
Piccolo Composite Made of Carbon Fibers Reinforced Polymer, CarboFix Orthopedics, Ltd., www.carbo-fix.com, Sep. 2011, 4 pp.
Darden Business Publishing—University of Virginia, UVA-QA-0811, Oct. 20, 2014, 10 pp.
IP-XS Nail Compression Nail System Surgical Technique and Product Information, Smith & Nephew GmBH, www.smith-nephew.de, Apr. 2004, 24 pp.
Trigen Intertan Intertrochanteric Antegrade Nail Surgical Technique, Smith & Nehew, Inc., www.smith-newphew.com, 2012, 46 pp.
S.S.T. Small Bone Locking Nail Fibula Nail Surgical Technique, Biomet, Inc., www.bioment.com, 12 pp.
MetaFLEX Percutaneous Flexible IM Nail System for Metacarpal and Metatarsal Fractures, Small Bone Innovtions, www.totalsmallbone.com, Apr. 2007, 2 pp.
Improved Healing of Clavicle Fractures using an Implantable Pre-Curved Intramedullary Rod, Upstate Medical University, www.upstate.edu, 1 pp.
The Titanium Flexible Humeral Nail System, Synthes (USA), Jul. 1999, 4 pp.
The Next Generation in Foot & Ankle Repair and Reconstruction Technology, Arthrex, www.arthrex.com, 2016, 76 pp.
Trim-It Drill Pin Fixation, , 1 pp.
Micronail II Intramedullary Distal Radius System Surgical Technique, Wright Medical Technology, Inc., www.wmt.com, Jun. 15, 2014, 20 pp.
Wrist Fracture Nail, Sonoma Orthopedic Products, Inc., www.sonomaorthopedics.com, 2013, 15 pp.
Supplementary Partial European Search Report dated Mar. 4, 2019 for corresponding European Patent Application No. EP16824907.

* cited by examiner

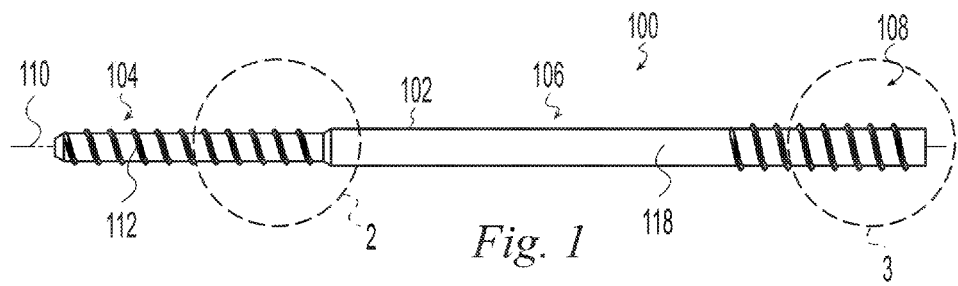
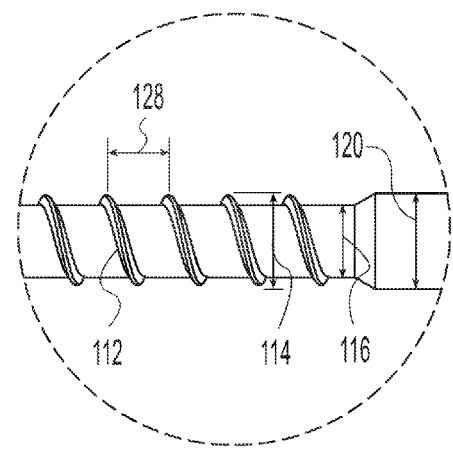
Fig. 2
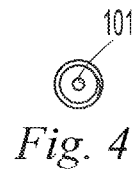
Fig. 4
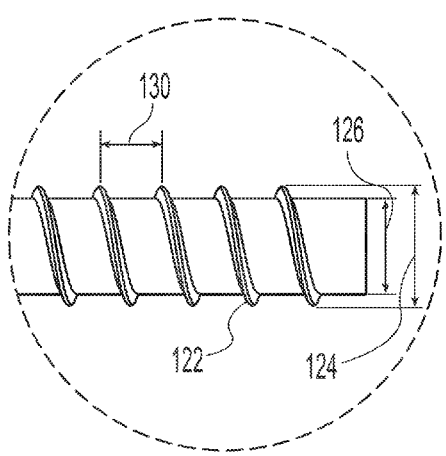
Fig. 3
Fig. 1

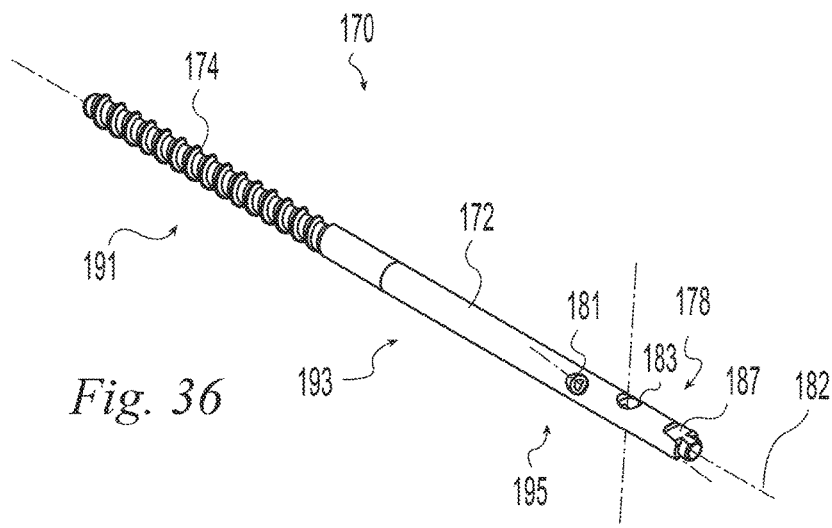
Fig. 36
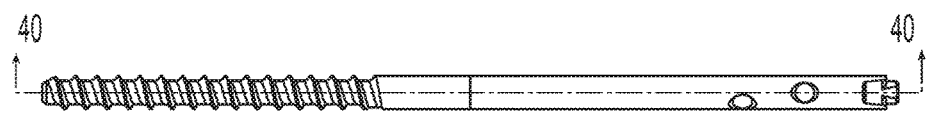
Fig. 37
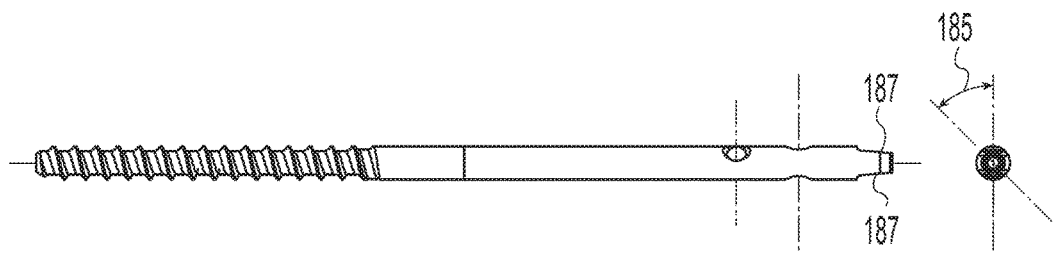 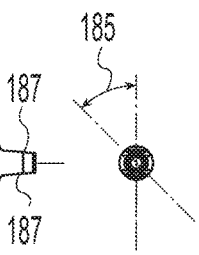
Fig. 38    Fig. 39

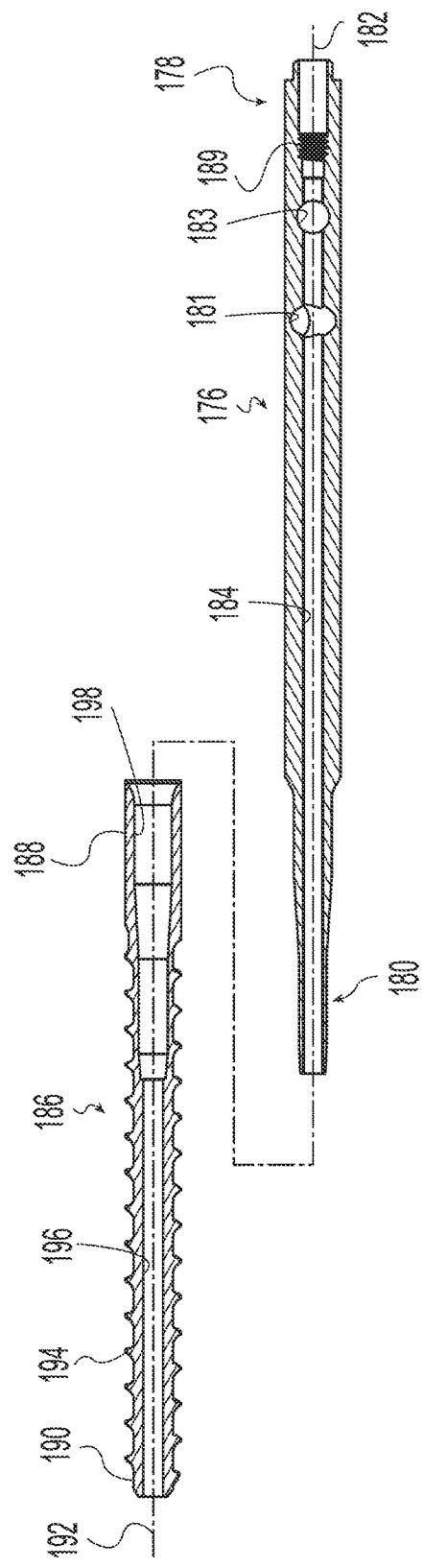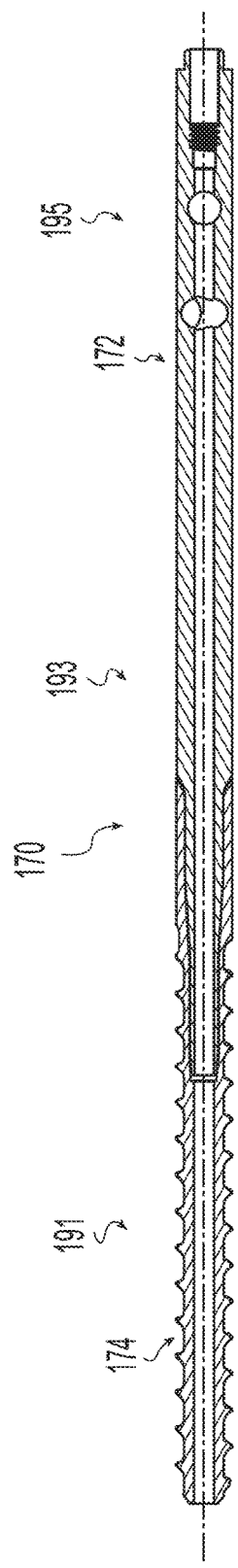
Fig. 41
Fig. 40

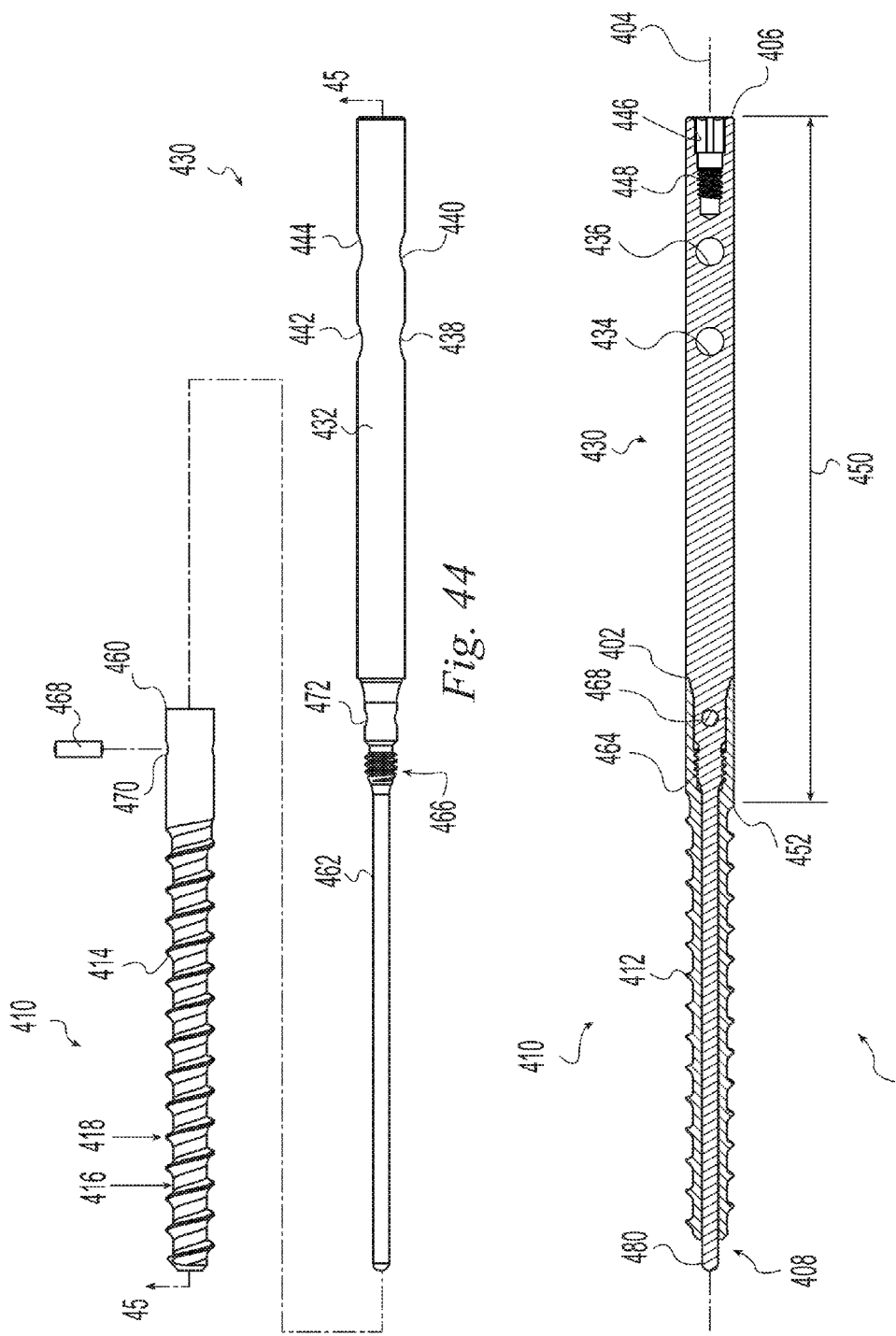

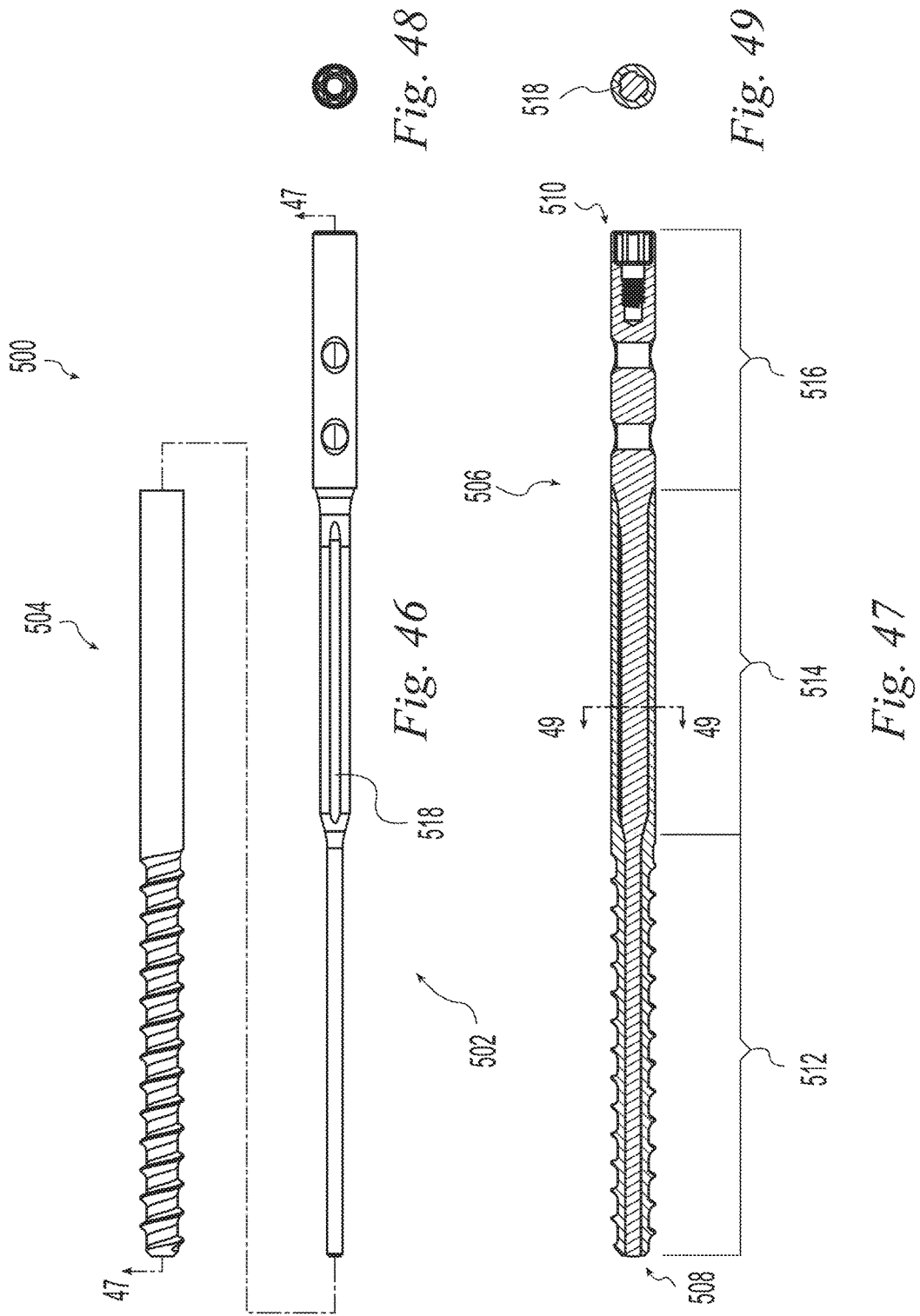

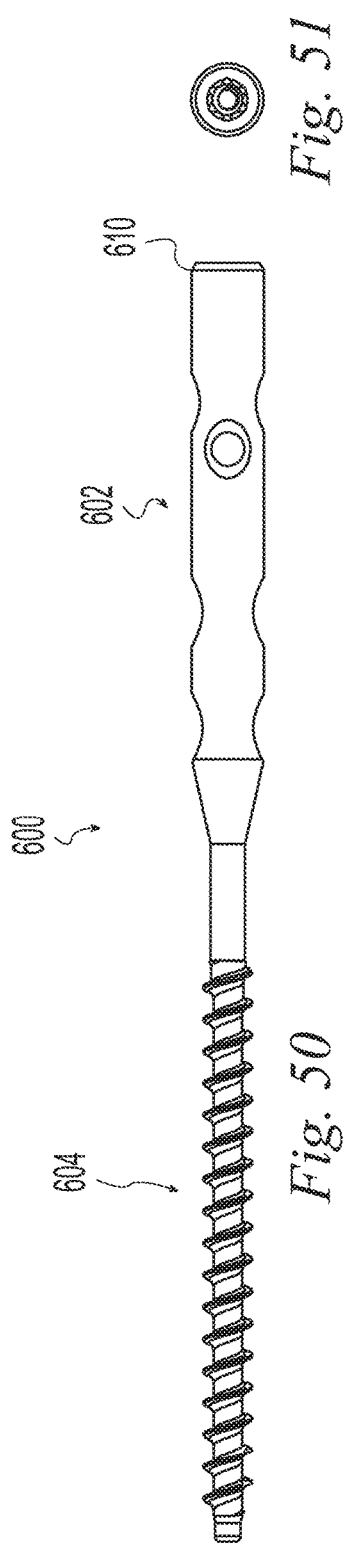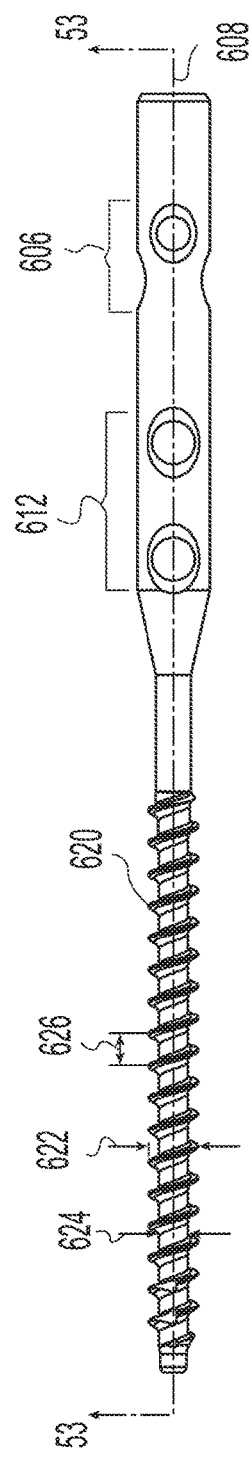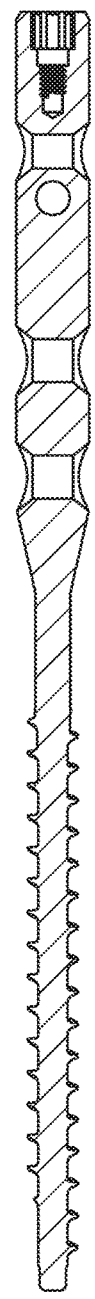
Fig. 50
Fig. 51
Fig. 52
Fig. 53

FLEXIBLE BONE IMPLANT

CROSS-REFERENCE TO RELATED APPLICATIONS

This application is a continuation-in-part of U.S. patent application Ser. No. 15/285,608, filed Oct. 5, 2016, which is a continuation-in-part of U.S. patent application Ser. No. 15/197,879, filed Jun. 30, 2016, which claims the benefit of U.S. Provisional Application No. 62/191,904, filed Jul. 13, 2015, and U.S. Provisional Application No. 62/238,780, filed Oct. 8, 2015, all of which are hereby incorporated by reference.

FIELD OF THE INVENTION

Examples of the invention relate generally to orthopedic devices for the surgical treatment of bone and, more particularly, to the stabilization of bones with an intramedullary device.

BACKGROUND

Orthopedic medicine provides a wide array of implants that can be attached to bone to repair fractures. External fixation involves the attachment of a device that protrudes out of the skin, and therefore carries significant risk of infection. Many fractures in long bones can be repaired through the use of bone plates, which are implanted and attached to lie directly on the bone surface. The bone plate then remains in the body long enough to allow the fractured bone to heal properly. Unfortunately, such bone plates often require the surgical exposure of substantially the entire length of bone to which the plate is to be attached. Such exposure typically results in a lengthy and painful healing process, which must often be repeated when the implantation site is again exposed to allow removal of the plate. There is a need in the art for implants and related instruments that do not require such broad exposure of the fractured bone, while minimizing the probability of infection by avoiding elements that must protrude through the skin as the bone heals.

SUMMARY

Examples of the invention provide devices and methods for stabilizing first and second bone portions relative to one another.

In one example of the invention, a bone implant for stabilizing bone fractures includes a body defining a longitudinal axis extending between a proximal end and a distal end. An elongate distal portion of the body has an outer surface defining a distal screw thread. The distal screw thread has a minor diameter and a major diameter. An elongate, headless, proximal portion of the body has a non-threaded outer surface having a diameter. The diameter of the proximal portion is greater than or equal to the major diameter of the distal screw thread.

In another example of the invention, a method of stabilizing a fractured long bone having an intramedullary canal includes: providing a bone implant comprising a body defining a longitudinal axis extending between a proximal end and a distal end; an elongate distal portion of the body having an outer surface defining a screw thread, the screw thread having a minor diameter and a major diameter; and an elongate, headless, proximal portion of the body having a non-threaded outer surface having a diameter, the diameter of the proximal portion being greater than or equal to the major diameter of the distal screw thread; and inserting the bone implant into an intramedullary canal of a bone so that the proximal portion spans a fracture in the bone.

BRIEF DESCRIPTION OF THE DRAWINGS

Various examples of the invention will be discussed with reference to the appended drawings. These drawings depict only illustrative examples of the invention and are not to be considered limiting of its scope.

FIG. 1 is a side elevation view of a bone implant according to one example of the invention;

FIG. 2 is a detail view of the bone implant of FIG. 1;

FIG. 3 is a detail view of the bone implant of FIG. 1;

FIG. 4 is an end view of the bone implant of FIG. 1;

FIG. 36 is a perspective view of a bone implant according to one example of the invention;

FIG. 37 is a top plan view of the bone implant of FIG. 36;

FIG. 38 is a side elevation view of the bone implant of FIG. 36;

FIG. 39 is an end view of the bone implant of FIG. 36;

FIG. 40 is a sectional view taken along line 40-40 of FIG. 37;

FIG. 41 is an exploded sectional view taken along line 40-40 of FIG. 37;

FIG. 44 is an exploded side view of a bone implant according to one example of the invention;

FIG. 45 is an assembled sectional view taken along line 45-45 of FIG. 44;

FIG. 46 is an exploded side view of a bone implant according to one example of the invention;

FIG. 47 is an assembled sectional view taken along line 47-47 of FIG. 46;

FIG. 48 is an end view of the bone implant of FIG. 46;

FIG. 49 is a cross sectional view taken along line 49-49 of FIG. 47;

FIG. 50 is a top view of a bone implant according to one example of the invention;

FIG. 51 is an end view of the bone implant of FIG. 50;

FIG. 52 is a front view of the bone implant of FIG. 50;

FIG. 53 is a cross sectional view taken along line 53-53 of FIG. 52;

DESCRIPTION OF THE ILLUSTRATIVE EXAMPLES

Figure 5:
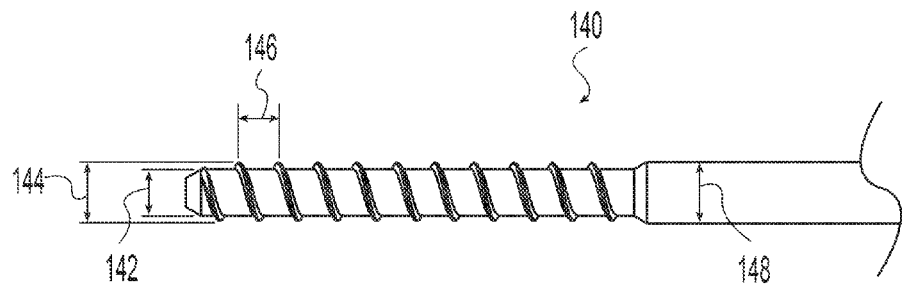
FIGS. 5-7 are side elevation views of a set of differently sized bone implants like that of FIG. 1.

The term "transverse" is used herein to mean not parallel. FIGS. 1-4 depict a bone implant 100 according to one example of the invention having an elongate body 102 with a distal portion 104, a mid-portion 106 and a proximal portion 108 spaced longitudinally relative to a longitudinal axis 110. The distal portion 104 includes a helical thread 112 having a major diameter 114, a minor diameter 116, and a pitch 128. The mid-portion 106 has a non-threaded outer surface 118 with an outer diameter 120. In the illustrative example of FIGS. 1-4, the mid-portion outer diameter 120 is equal to or greater than the thread major diameter 114. The distal threaded portion 104 is operable to bend as it is threaded into a bone to follow a curved path. For example, the bending stiffness of the distal threaded portion 104 is such that it will bend to follow a curved path in human bone. Such a curved path may be defined, for example, by a curved hole in the bone, a guide wire, or a natural bone feature such as a non-linear intramedullary canal bounded by cortical bone. This is distinct from prior art threaded implants which if started on a curved path in human bone would, when advanced, continue in a straight line and thus deviate from the curved path and form their own, straight, path through the bone. Preferably the bending stiffness of the threaded distal portion 104 is lower than the bending stiffness of the mid-portion 106. The relatively lower bending stiffness of the threaded distal portion 104 causes the threaded distal portion to bend to follow a curved path while the relatively higher bending stiffness of the mid-portion causes the mid-portion to remain straight to stabilize first and second bone portions relative to one another at a bone interface such as at a fracture, osteotomy, or fusion site. The difference in bending stiffness between the threaded distal portion 104 and the mid-portion 106 may be achieved in different ways. For example, the threaded distal portion 104 and the mid-portion 106 may be made of different materials and/or may have different sectional moduli. In the illustrative example of FIGS. 1-4, the threaded distal portion 104 and the mid-portion 106 have different sectional moduli. The threaded distal portion minor diameter 116 is less than the outer diameter 120 of the mid-portion 106 and the threaded distal portion major diameter is less than or equal to the outer diameter 120 of the mid-portion 106. Preferably, the ratio of the bending stiffness of the mid-portion 106 to the bending stiffness of the threaded distal portion 104 is in the range of 1.5:1 to 100:1. More preferably, the ratio is in the range of 2:1 to 20:1. For example, implants according to examples of the present invention and suitable for internal fixation of a clavicle fracture and that fall within these ranges may have a major diameter 114 in the range of 4-6.5 mm, a minor diameter 116 in the range of 2.5-3.5 and a cannulation 101 with a diameter in the range of 1-2 mm. Preferably, the implant 100 is made of a polymer.

Table 1 compares the calculated load required to bend a cantilevered tube of 3 mm outside diameter and 1.5 mm inside diameter around a radius of 50 mm and an arc length of 26 mm for different materials. The titanium and stainless steel alloys are predicted to have a required load approximately 10 times that of the PEEK and PLLA. These loads would be greater than the bone could withstand and a threaded device made of those materials would not follow a curved path in the bone but would instead cause the bone to fail. In the case of the highly cold worked stainless steel, even if the bone could withstand the load, the implant would fail since the minimum bend radius before failure of the implant is greater than 50 mm.

TABLE 1

Load at 50 mm bend radius

| Material | Yield Stress (MPa) | Failure Stress (MPa) | Yield Strain (%) | Failure Strain (%) | Flexural Modulus (MPa) | Load (N) |
|---|---|---|---|---|---|---|
| PEEK ASTM F2026 | 100 | 115 | 2.5% | 20% | 4 | 9.8 |
| PLLA | 90 | 100 | 2.6% | 25% | 3.5 | 8.7 |
| Ti—6Al—4V ELI ASTM F136 | 880 | 990 | 0.8% | 14% | 114 | 91.7 |
| 316LVM Stainless Steel ASTM F899 | 1468 | 1696 | 0.7% | 3% | 197 | Not possible |

Another way to quantify the bending stiffness of the threaded distal portion 104 is by the amount of torque required to turn the threaded distal portion 104 into a curved bone hole having a specified radius of curvature. For example, the threaded distal portion 104 preferably requires a torque less than 20 in-lbs to turn the distal threaded portion 104 into a bone to follow a curved path having a radius of curvature of 50 mm. More preferably the required torque is less than 10 in-lbs. More preferably the required torque is less than 5 in-lbs. More preferably the required torque is approximately 2 in-lbs.

Table 2 compares the measured torque required to advance a threaded tube 25 mm into a 50 mm threaded radius formed in a rigid test block. The tubes were all machined to the same geometry but of different materials. The thread major diameter was 4.25 mm, the minor diameter was 3.0 mm and the inner diameter of the tube was 1.5 mm. A rigid block was prepared having a curved, threaded path. Such a path has a pitch that is wider on the outside of the curve and a pitch that is narrower on the inside of the curve corresponding to the shape of the thread when it is curved. Multiple samples of each tube were inserted into the block over an arc length of 25 mm. The maximum torque for each revolution was measured and it was found that the torque increased for each revolution. In Table 2, the range is the range of torque values from the first to the last revolution. The average is the average of the torque values for all revolutions. The peak is the highest torque value and in all cases occurred in the last revolution. However, the torque values for each material were relatively constant over the last few revolutions. The titanium and stainless steel alloys had measured torque values approximately 10 times that of the PEEK. These tests were conducted using a threaded block made of tool steel with a strength greater than that of the materials being tested in order to compare the torque values. As pointed out relative to Table 1, the loads generated from the metal implants would be greater than the bone could withstand and a threaded device as described herein made of these metals would not follow a curved path in the bone but would instead cause the bone to fail.

TABLE 2

Torque to thread around rigid 50 mm radius

| Material | Range (in-lbs) | Average (in-lbs) | Peak (in-lbs) |
|---|---|---|---|
| PEEK ASTM F2026 | 0-2.0 | 1.4 | 2.0 |
| Ti—6Al—4V ELI ASTM F136 | 0.7-25 | 16 | 25 |

TABLE 2-continued

Torque to thread around rigid 50 mm radius

| Material | Range (in-lbs) | Average (in-lbs) | Peak (in-lbs) |
|---|---|---|---|
| 316LVM Stainless Steel ASTM F899 | 0.5-20 | 13 | 20 |

In addition to bending stiffness advantages, having the threaded distal portion major diameter less than or equal to the outer diameter 120 of the mid-portion 106 allows the distal threaded portion 104 to pass through a passage in a bone that will be a sliding or press fit with the mid-portion 106. A bone implant so configured, as shown in the illustrative example of FIGS. 1-4, can have an intramedullary canal filling mid-portion 106 providing solid support to a bone interface and a relatively bendable distal threaded portion 104 following a curved path such as for threading into a distal portion of a curved bone to secure the implant in the bone.

The proximal portion 108 may be identical to the mid-portion 106. Alternatively, the proximal portion may have a positive driver engagement feature (not shown) such as internal or external non-circular surfaces, profiles, or holes. For example, an internal or external slotted, threaded, triangular, square, hexagonal, hexalobular, or other drive feature may be provided. In addition, as shown in the illustrative example of FIGS. 1-4, the proximal portion 108 may include an optional external helical thread 122 able to engage a bone portion to provide proximal fixation of the implant. For example, the proximal thread 122 may have a major diameter 124, a minor diameter 126, and a pitch 130. In the illustrative example of FIGS. 1-4, the mid-portion outer diameter 120 is equal to the proximal thread minor diameter 126 and the distal thread major diameter 114. The proximal portion may alternatively, or in addition, receive a locking member such as a pin or screw transverse to the longitudinal axis to lock a proximal bone portion to the nail. The locking member may be drilled through the proximal portion. Preferably, the proximal portion has one or more transverse holes formed through it for receiving the locking member.

The distal and proximal thread pitches 128, 130 may advantageously be the same or different depending on the application. For example, to stabilize a fracture, the implant 100 may be inserted into a bone across the fracture so that the distal thread 112 is engaged with bone distal to the fracture and the proximal thread 122 is engaged with bone proximal to the fracture. If the bone portions on either side of the fracture are reduced to a desired final position prior to inserting the implant 100, then it is advantageous for the thread pitches 128, 130 to be equal so that insertion of the implant does not change the relative positions of the bone portions. If on the other hand, it is desirable to move the bone portions relative to one another by the action of inserting the implant then it is advantageous for the pitches 128, 130 to be different. For example, to move the bone portions closer together to reduce the fracture, the distal thread pitch 128 may be made greater than the proximal thread pitch 130 so that with the distal thread 112 engaged distally and the proximal thread 122 engaged proximally, further advancing the implant causes the distal bone portion to move proximally relative to the implant faster than the proximal bone portion moves proximally and thus move the bone portions closer together. Alternatively, to move the bone portions further apart to distract the fracture, the distal thread pitch 128 may be made smaller than the proximal thread pitch 130 so that with the distal thread 112 engaged distally and the proximal thread 122 engaged proximally, further advancing the implant causes the distal bone portion to move proximally relative to the implant more slowly than the proximal bone portion moves proximally and thus move the bone portions further apart. Preferably, the bone implant 100 has a through bore, or cannulation 101, coaxial with the longitudinal axis 110 to permit the bone implant 100 to be inserted over a guide wire.

Figure 6:
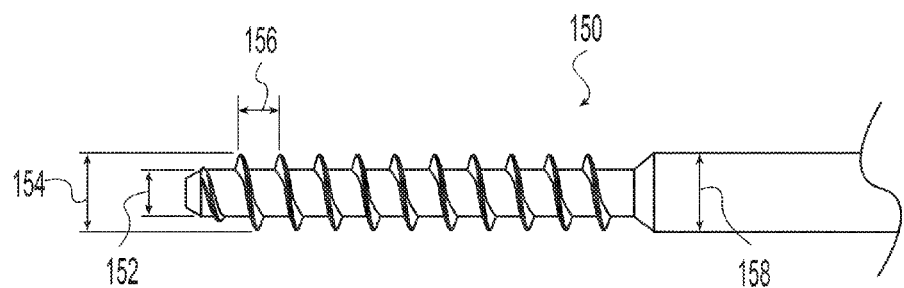
Figure 7:
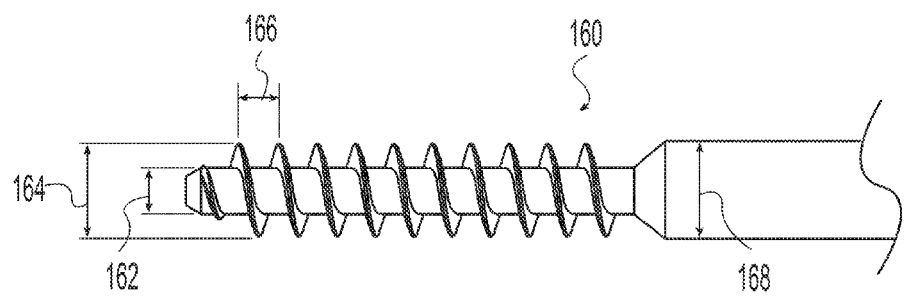

The bone implant 100 of FIGS. 1-4, may advantageously be provided in a set containing a plurality of threaded implants as shown in the illustrative example of FIGS. 5-7. For example, it is advantageous in a surgical procedure to minimize the number of steps and the amount of time needed to complete the procedure. In a bone fixation procedure, a surgeon often makes an initial sizing decision based on medical imaging. During the procedure, it may become expedient to change the predetermined size based on observation of the surgical site or the fit of trial implants or instruments. For example, a surgeon may determine initially that a smaller threaded implant is appropriate. However, during preparation of the site, the surgeon may determine that a larger threaded will better grip the bone or fill, for example, a canal in the bone. The illustrative set of implants shown in FIGS. 5-7 facilitates changing between sizes. Each implant thread 140, 150, 160 in the set has a minor diameter 142, 152, 162, a major diameter 144, 154, 164, and a pitch 146, 156, 166. The minor diameters 142, 152, 162 are equal to one another so that a single diameter drill will provide an initial bore hole appropriate for all the threads in the set. The pitches 146, 156, 166 are equal to one another so that all of the threads in the set will threadably engage a helical thread of the same pitch. The major diameters 144, 154, 164 may increase to provide progressively more bone purchase or, for example, to span increasing larger intramedullary canals. For example, with the set of implants of the illustrative example of FIGS. 5-7, a surgeon may drill a hole equal to the minor diameters 142, 152, 162 and then tap the hole with a tap corresponding to the thread of the smallest major diameter thread 140. The tactile feedback received by the surgeon as the tap is inserted will indicate to the surgeon if the thread major diameter is sufficient to provide a desired level of bone engagement. For example, the surgeon can feel if the tap is engaging the cortical walls of an intramedullary canal or if the tap is in softer cancellous bone. If the surgeon determines that greater engagement is desired, the surgeon can next tap the hole with a tap corresponding to the thread of the next larger major diameter thread 150. Since the minor diameters 142, 152, 162 and thread pitches 146, 156, 166 are the same for all of the implants in the set, the next tap will thread into the previously tapped hole and increase the bone thread major diameter without damaging the bone thread. Once the desired bone engagement is achieved, the surgeon may then insert the desired implant 140, 150, 160. If in tapping the larger major diameter thread, the surgeon determines that the bone is providing too much resistance, the surgeon may revert to the smaller sized implant since the threads are still compatible. Alternatively to using a separate tap, the screw threads may be configured as self-tapping so that the implants may be threaded directly into the bored hole.

In addition to the sizing advantages of having the same minor diameter 142, 152, 162 across a family of implants, it is also advantageous because the distal threaded portion of each implant will have a similar bending stiffness to each of the other implants 140, 150, 160 since the continuous wall of the minor diameter contributes much more to the bending stiffness than the helical thread itself. This similar bending stiffness means that they can be inserted around a similar bending radius with a similar torque.

In the illustrative example of FIGS. 5-7, each implant 140, 150, 160 has a mid-portion diameter 148, 158, 168 equal to the corresponding major diameter 144, 154, 164. The increasing mid-portion diameters provide progressively less flexible mid-portions across the set of implants and, for example, canal filling for increasingly larger bones if used in the intramedullary canal. If the implants incorporate the optional increasing mid-portion diameter as shown, then it is desirable to re-drill the mid-portion of the bone hole to accommodate the mid-portion when an increase in implant size is desired. However, the distal, threaded portion of the bone hole does not need to be re-drilled so the implant threads will not be damaged by drilling. The mid-portion diameter may also be larger than the corresponding distal thread major diameter to further increase the mid-portion stiffness.

Alternatively to, or in addition to, the threaded distal portion 104 and mid-portion 106 having different sectional moduli, the threaded distal portion 104 and mid-portion 106 may have different material properties such as two different materials or different conditions of the same material to produce a difference in bending stiffness between them.

In the illustrative example of FIGS. 36-41, an implant 170 has separate first and second members 172, 174 permanently joined together. The first member 172 includes an elongate body 176 with a proximal end 178, a distal end 180, a longitudinal axis 182, and an axial through bore 184. The proximal end 178 of the first member includes a pair of transverse through bores 181, 183. Each transverse bore 181, 183 defines a longitudinal axis and the axes form an angle 185 between them about the longitudinal axis 182 as best seen in FIG. 39. Providing more than one transverse through bore increases options for attaching the implant to bone fragments and options for fixation direction. Both bores may be used for fixation or the one that is most conveniently located may be used. Preferably the angle 185 is in the range of 0 to 90 degrees. More preferably the angle 185 is in the range of 20 to 90 degrees. In the illustrative example of FIGS. 36-41, the angle 185 is 45 degrees. The proximal end 178 also includes opposed flats 187 for engaging a driver in torque transmitting relationship. An internal thread 189 within the bore 184 is engageable with, e.g., a threaded draw bar to secure the first member to a driver.

The second member 174 includes an elongate body 186 with a proximal end 188, a distal end 190, a longitudinal axis 192, an external helical thread 194, and an axial through bore 196. The distal end 180 of the first member 172 and the proximal end 188 of the second member 174 may have complementary geometries to aid in joining them. In the illustrative example of FIGS. 36-41, the distal end 180 of the first member has a stepped conical taper and the proximal end 188 of the second member has a corresponding stepped conical socket 198. The mating surfaces may be any suitable shape as determined by the materials and joining technique including but not limited to plug and socket joints (as shown), scarf joints, butt joints, dovetail joints, finger joints, and lap joints. The joint may be reinforced with a third component such as an adhesive, pin, or key. The joint may be formed by mechanical interlock, chemical bonding, molding, welding or other suitable joining process. The final assembled implant 170, has a distal portion 191, a mid-portion 193 and a proximal portion 195 and may have the thread forms, diameters, and relationships as described relative to the examples of FIGS. 1-7.

The first and second components 172, 174 may be made of different materials or different conditions of the same material. For example, they may be made of polymers, metals, or ceramics. Metals may include stainless steel alloys, titanium, titanium alloys, cobalt-chromium steel alloys, nickel-titanium alloys, and/or others. Polymers may include nonresorbable polymers including polyolefins, polyesters, polyimides, polyamides, polyacrylates, poly(ketones), fluropolymers, siloxane based polymers, and/or others. Polymers may include resorbable polymers including polyesters (e.g. lactide and glycolide), polyanhydrides, poly (aminoacid) polymers (e.g. tyrosine based polymers), and/or others. Other possible materials include nonresorbable and resorbable ceramics (e.g. hydroxyapatite and calcium sulfate) or biocompatible glasses. They may be made of homogenous materials or reinforced materials. They may be made of crystallographically different materials such as annealed versus cold worked. It is preferable for the mid portion 193 and proximal portion 195 to have a higher bending stiffness than the distal portion 191 and the distal portion preferably has a bending stiffness low enough for it to be inserted along a curved path in bone.

In a first example, the first component may be made of a metal with a relatively high degree of cold work and the second component of a metal with a relatively low amount of cold work such as for example annealed and cold worked stainless steel. The components may be joined for example by welding. However, as discussed relative to Table 1, most metals are far too stiff to allow threading along a curved path in a bone within suitable torsional loads.

Preferably the distal portion is made of a polymer. In a second example, the first component is made of a metal, such as stainless steel or a titanium alloy, and the second component is made of a polymer such as polyetheretherketone (PEEK) or a polylactide polymer (e.g. PLLA). The components may be joined such as for example by threading them together.

Preferably both components are made of polymers. In a third example, the first and second components are both made of non-resorbable polymers. For example, the first component may be made of fiber reinforced PEEK (e.g. Invibio PEEK-Optima™ Ultra-Reinforced) and the second component may be made of neat (unreinforced) PEEK (e.g. Invibio PEEK-Optima™ Natural). The fiber reinforced PEEK is strong while the neat PEEK is relatively flexible allowing it to be easily threaded around a curved path even while having a relatively large bone filling diameter. The components may be joined, e.g. by molding the components as a continuous matrix with first component fiber reinforcement and second component neat polymer with polymer chains extending across the joint interface. In the example of FIGS. 36-41, the second component is relatively more transparent to laser radiation than the first component and the parts are joined by laser welding at the conical interface. The laser energy passes relatively easily through the second component and is absorbed by the first component so that localized heating at the conical interface takes place causing the polymer constituent of the two components to fuse together.

In a fourth example, the first and second components are made of resorbable polymers. For example, the mid-portion may be made of a glass fiber reinforced PLLA (e.g. Corbion-Purac FiberLive™) and the distal portion may be made of neat PLLA.

Alternatively, the first member 172 and second member 174 may form one continuous part with different properties between first and second portions. The difference in properties may be achieved, for example, by different processing (e.g. thermal processing) or blending materials. For example, different polymers may be combined in a single injection mold cavity and formed together. The polymers may be blended so that there is a transition between them. In another example, stiffening and/or strengthening material, e.g. fibers, whiskers, and/or granules, may be selectively incorporated in, e.g., the first portion.

Figure 43:
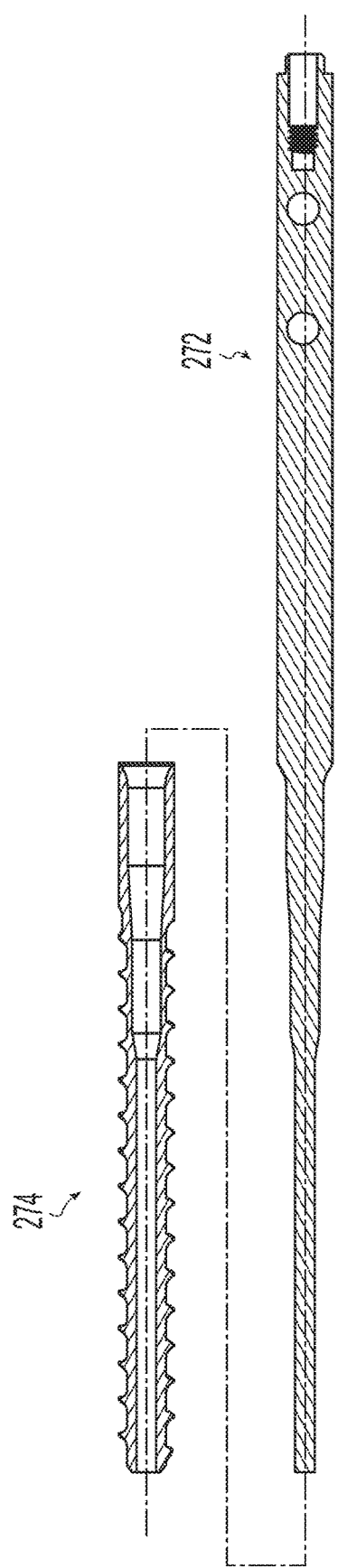
FIG. 43 is an exploded cross sectional view of the bone implant of FIG. 42.
Figure 42:
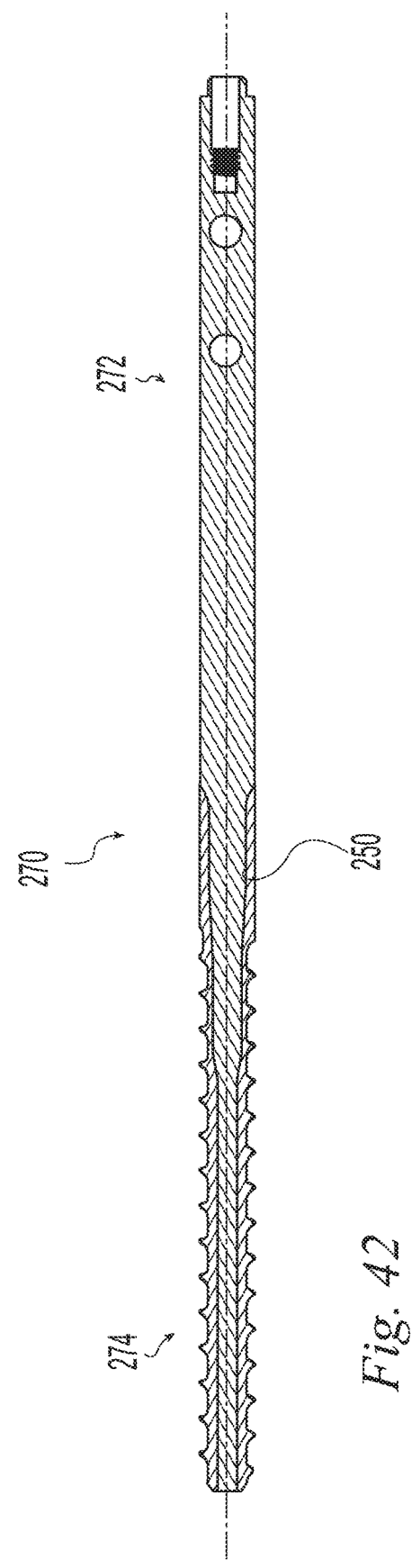
FIG. 42 is a cross sectional view of a bone implant according to one example of the invention.

FIGS. 42 and 43 illustrate an example of an implant 270 similar to that of FIGS. 36-41 except that the first member 272 is not cannulated, the first member 272 extends the full length of the second member 274, and the transverse holes 281, 283 are coplanar. The implant 270 may be assembled as with the prior example including by using complimentary screw threads in the proximal region of the second member 274 and mid portion of the first member 272 as indicated by reference number 250. The implant 270 of the example of FIGS. 42 and 43 may be include any of the materials and features described relative to the prior examples. If, for example, the first member 272 is made of a radiographically more opaque material than the second member 274, then the first member will provide a radiographic marker over the entire length of the screw 270 that may be radiographically visualized during and after surgery to confirm implant placement. For example, a metal first component and polymer second component would provide for radiographic visualization of the metal first component. It has been found by the present inventors that the bending stiffness of the distal end of the implant is not materially changed by eliminating the axial through bore of the first component and is essentially unchanged when the bending stiffness of a guide wire is accounted for which was optionally used with the previous cannulated implant examples. The guide wire is not necessary inasmuch as the implant 270 will follow a curved path receiving it. The transverse holes 181, 183 may be provided in any number or not at all as desired but it has been found that one is sufficient and two provides the user with additional fixation choice.

FIGS. 44 and 45 illustrate a bone implant 400 useful for stabilizing bone fractures according to one example of the invention. The bone implant 400 includes a body 402 defining a longitudinal axis 404 extending between a proximal end 406 and a distal end 408. The body has an elongate distal portion 410 having an outer surface 412 defining a screw thread 414 having a minor diameter 416 and a major diameter 418. The body has an elongate proximal portion 430 having a non-threaded outer surface 432. Passages 434 and 436 are each formed through the proximal portion 430 transverse to the longitudinal axis from a first opening 438, 440 on the surface of the proximal portion to a second opening 442, 444 on the surface of the proximal portion. A driver engaging feature is formed at the proximal end for engaging a driver in torque transmitting relationship. The driver engaging feature may be a male feature or a female feature. Preferably it is a polygonal feature engageable with a correspondingly shaped driver. In the example of FIGS. 44 and 45, the driver engaging feature is a hexagonal socket 446 formed in the proximal end of the implant. The socket 446 includes a threaded recess 448 for threaded engagement with other tools such as a driver retaining draw rod, a cross pinning guide, or the like. The distal portion is responsive to rotation of the implant to thread into a bone and advance the bone implant into the bone. This rotary advancement action is advantageous compared to typical bone nails that are impacted into the bone since the threaded advancement is less stressful to the bone and surrounding tissues. As the distal portion is threaded into the bone, it pulls the proximal portion into the bone. The distal threaded portion is anchored in the bone by the thread 414. The smooth proximal portion may be positioned to span a fracture so that, for example, no sharp edges are engaged with the fracture and no stress concentrating features that might weaken the implant span the fracture.

In the example of FIGS. 44 and 45, the proximal portion has a length 450 measured from the free proximal end 406 to the proximal start 452 of the threads of the distal portion. The proximal portion has a maximum diameter. For example for a conical or cylindrical proximal portion the maximum diameter is simply the largest diameter along the proximal portion. For an ovoid proximal portion, the maximum diameter would be the major diameter of the elliptical cross section. For other shapes, such as fluted proximal portions, the maximum diameter is the maximum dimension normal to the longitudinal axis 404 of the proximal portion. The maximum diameter is preferably constant over a portion of the proximal portion length to provide a uniform thickness for spanning a fracture. For example, the maximum diameter is preferably uniform over at least one-fourth of the proximal portion length; more preferably at least one-third; more preferably at least one-half; more preferably more than one-half. In the illustrative example of FIGS. 44 and 45, the proximal portion has a constant cylindrical diameter over its entire length. The driver engaging feature preferably has a maximum dimension normal to the longitudinal axis that is less than or equal to the maximum diameter of the proximal portion so that, for example, the proximal end of the bone implant may be seated below the bone surface.

The bone implant may be a unitary construct, like shown in the illustrative example of FIGS. 1-4, in which the proximal and distal portions are formed of one continuous material. Optionally, the proximal and distal portions may be separate components joined together as shown in the example of FIG. 36 and the example of FIG. 42. In the illustrative example of FIGS. 44 and 45, the bone implant includes a sleeve 460 surrounding a separate core 462. The sleeve and core are joined together to form the body. Various methods may be used to join the sleeve and core. For example, they may be threaded, pinned, bonded, welded, or otherwise joined. In the example of FIGS. 44 and 45, the sleeve is threaded onto the core via an internal thread 464 and corresponding male thread 466 formed on the core. The sleeve is further pinned to the core with a pin 468 pressed through holes 470, 472 in the sleeve wall and in the core.

As described relative to previous examples, it is desirable for the distal portion to have a lower bending resistance than the proximal portion. In one example, the sleeve is at least partially formed of a polymer and the core is at least partially formed of a metal. In the example of FIGS. 44 and 45, the sleeve is machined from a polymer and includes the distal screw thread while the core is machined from a metal and includes the proximal portion. In one example, the core is made of a biocompatible titanium alloy and the sleeve is made of a biocompatible poly(ketone) polymer such as, for example, polyetheretherketone. In another example, the core is made of a suitable biocompatible metal and the sleeve is made of a resorbable polymer so that, over time, the sleeve will resorb in the patient's body and allow gradually increasing motion of the bone and load transfer to the bone to promote healing. The core may extend partway toward the distal end as in the example of FIG. 36, all the way to the distal end as in the example of FIG. 42, or it may extend past the distal end as in the example of FIGS. 44 and 45. With the tip 480 of the core extending beyond the distal end, the tip 480 provides an easier start of the implant into a hole in the bone and, as shown in the example of FIGS. 44 and 45, the tip 480 provides a smooth bearing surface for following a curved path in a bone.

FIGS. 46 through 49 illustrate a bone implant 500 similar to that of FIGS. 44 and 45. The bone implant 500 includes a core 502 and a sleeve 504. In the example of FIGS. 44 and 45, the smooth proximal portion 506 is more evenly proportioned over the core and sleeve. Also, the core steps up more gradually in diameter from the distal end 508 to the proximal end 510 resulting in a more gradual transition in bending stiffness over three zones. In a first zone 512, a relatively thin portion of the core is surrounded by a relatively thick portion of the sleeve. In a second zone 514, a relatively thicker portion of the core is surrounded by a relatively thinner portion of the sleeve. In a third zone 516, only a relatively thicker portion of the core remains. Also, in the example of FIGS. 46 through 49 a slip resisting feature is provided on the core and a polymer sleeve is molded to the core so that the polymer and slip resisting feature interdigitate. The slip resisting feature may be knurling, threads, grooves, splines, spikes, holes, or other features. The slip resisting feature may be oriented to enhance torque transfer, longitudinal force transfer, or otherwise oriented. In the example of FIGS. 46 and 47, the slip resisting feature includes longitudinal splines 518 to enhance the ability to transfer torque between the core and sleeve. Longitudinal force transfer is sufficiently accommodated by the bonding of the sleeve to the core during the molding process.

In use, the preceding implants may be provided in an appropriate size and inserted into a bone to span a fracture in the bone. Preferably the proximal portion of the implant spans the fracture. The arrangement of a smooth proximal portion and a threaded distal portion permits rotating the bone implant to cause the threaded distal portion to engage the bone and pull the proximal portion of the bone implant into a positioning spanning the fracture. In the case of an implant comprising a resorbable polymer, the polymer will resorb over time in the patient to gradually transfer load to and permit motion of the bone to enhance healing of the fracture. One or more pins or screws may be inserted so that they extend through one or more of the passages in the proximal end and through a portion of the bone to fix the bone to the proximal portion of the implant. For example with the distal end of the bone implant fixed by engagement of the distal threads in a distal portion of the bone a proximal portion of the bone may be secured with pins or screws as described. This may be used to hold compression or distraction on bone portions on opposing sides of the fracture or to attach loose bone fragments.

FIGS. 50-53 illustrate a bone implant 600 similar to the preceding examples inasmuch as it has a smooth rod-like proximal portion 602 and a threaded distal portion 604. The proximal portion 602 has one or more transverse passages through the proximal portion, each passage extending from a first opening on the surface of the proximal portion to a second opening on the surface of the proximal portion. The distal portion may be threaded into a bone to secure the implant 600 to the bone at the distal end. The proximal portion, is preferably positioned to bridge a fracture to provide support to the fracture while the fracture heals. The transverse passages can receive a fastener such as a pin, wire, screw or the like to connect the proximal portion to bone. In the illustrative example of FIGS. 50-53, the implant 600 is configured for placement in the intramedullary canal of a fibular bone to support a fracture of the fibular bone and optionally to support screws for reinforcing the syndesmosis joint of an ankle. The proximal portion includes a first pair of holes 606 perpendicular to the implant longitudinal axis 608 and angled relative to one another about the axis 608. The first pair of holes 606 is positioned nearer the proximal end 610 of the implant to receive fasteners for attaching the implant 600 to a portion of the bone, or fragment, proximal to a fracture. The implant further includes a second pair of holes 612 perpendicular to the implant longitudinal axis and, in this example, parallel to one another. The second pair of holes 612 is positioned distal to the first pair and is arranged to receive fasteners that extend through the fibula and into the tibia to reinforce the syndesmosis joint. In the illustrative example of FIGS. 50-53 the implant 600 is a unitary construction. In other embodiments, the implant 600 may include a greater or a lesser number of transverse holes or no holes at all. The transverse holes may be perpendicular to the axis 608 as shown or at any other angle suitable for the target anatomy. The implant may be made of two or more parts joined together as in the previous examples. The distal portion 604 includes a distal thread 620 having a major diameter 622, a minor diameter 624, and a pitch 626.

The various examples according to the invention have a decreased bending stiffness of the distal portion relative to the proximal portion using various strategies including different section moduli and different materials. It is desirable for the distal thread to have a lower bending stiffness than conventional bone screws of a similar major diameter. In the illustrative examples, the bending stiffness of the distal portion may be lowered by utilizing a novel screw thread. For example, a thread according to an example of the invention has a smaller minor diameter and/or a larger pitch than a conventional bone screw thread. Table 3 compares illustrative examples of screw thread geometry according to examples of the invention to the industry standard bone screw threads described in ASTM F543.

TABLE 3

Screw thread geometry - Dimensions in mm

| A Thread | B Maj. dia. max | C Maj. dia. min | D Min. dia. max | E Min. dia. min | F Pitch | B/E ratio | C/D ratio | B/F ratio | C/F ratio | D/F ratio | E/F ratio |
| --- | --- | --- | --- | --- | --- | --- | --- | --- | --- | --- | --- |
| ASTM HA 1.5 | 1.50 | 1.35 | 1.10 | 1.00 | 0.50 | 1.50 | 1.23 | 3.00 | 2.70 | 2.20 | 2.00 |
| ASTM HA 2.0 | 2.00 | 1.85 | 1.30 | 1.20 | 0.60 | 1.67 | 1.42 | 3.33 | 3.08 | 2.17 | 2.00 |
| ASTM HA 2.7 | 2.70 | 2.55 | 1.90 | 1.75 | 1.00 | 1.54 | 1.34 | 2.70 | 2.55 | 1.90 | 1.75 |
| ASTM HA 3.5 | 3.50 | 3.35 | 2.40 | 2.25 | 1.25 | 1.56 | 1.40 | 2.80 | 2.68 | 1.92 | 1.80 |
| ASTM HA 4.0 | 4.00 | 3.85 | 2.90 | 2.75 | 1.50 | 1.45 | 1.33 | 2.67 | 2.57 | 1.93 | 1.83 |
| ASTM HA 4.5 | 4.50 | 4.35 | 3.00 | 2.85 | 1.75 | 1.58 | 1.45 | 2.57 | 2.49 | 1.71 | 1.63 |

TABLE 3-continued

Screw thread geometry - Dimensions in mm

| A Thread | B Maj. dia. max | C Maj. dia. min | D Min. dia. max | E Min. dia. min | F Pitch | B/E ratio | C/D ratio | B/F ratio | C/F ratio | D/F ratio | E/F ratio |
|---|---|---|---|---|---|---|---|---|---|---|---|
| ASTM HA 5.0 | 5.00 | 4.85 | 3.50 | 3.35 | 1.75 | 1.49 | 1.39 | 2.86 | 2.77 | 2.00 | 1.91 |
| ASTM HB 4.0 | 4.00 | 3.85 | 1.90 | 1.75 | 1.75 | 2.29 | 2.03 | 2.29 | 2.20 | 1.09 | 1.00 |
| ASTM HB 6.5 | 6.50 | 6.35 | 3.00 | 2.85 | 2.75 | 2.28 | 2.12 | 2.36 | 2.31 | 1.09 | 1.04 |
| ASTM HC 2.9 | 2.90 | 2.79 | 2.18 | 2.03 | 1.06 | 1.43 | 1.28 | 2.74 | 2.63 | 2.06 | 1.92 |
| ASTM HC 3.5 | 3.53 | 3.43 | 2.64 | 2.51 | 1.27 | 1.41 | 1.30 | 2.78 | 2.70 | 2.08 | 1.98 |
| ASTM HC 3.9 | 3.91 | 3.78 | 2.92 | 2.77 | 1.27 | 1.41 | 1.29 | 3.08 | 2.98 | 2.30 | 2.18 |
| ASTM HC 4.2 | 4.22 | 4.09 | 3.25 | 2.95 | 1.27 | 1.43 | 1.26 | 3.32 | 3.22 | 2.56 | 2.32 |
| ASTM HD 4.0 | 4.03 | 3.97 | 2.95 | 2.89 | 1.59 | 1.39 | 1.35 | 2.53 | 2.50 | 1.86 | 1.82 |
| ASTM HD 4.5 | 4.53 | 4.47 | 2.95 | 2.89 | 2.18 | 1.57 | 1.52 | 2.08 | 2.05 | 1.35 | 1.33 |
| Example 1 | 3.55 | 3.45 | 2.05 | 1.95 | 2.75 | 1.82 | 1.68 | 1.29 | 1.25 | 0.75 | 0.71 |
| Example 2 | 3.25 | 3.10 | 1.50 | 1.35 | 2.25 | 2.41 | 2.07 | 1.44 | 1.38 | 0.67 | 0.60 |
| Example 3 | 5.25 | 5.10 | 3.00 | 2.85 | 2.75 | 1.84 | 1.70 | 1.91 | 1.85 | 1.09 | 1.04 |

Column A is a description of each of the threads being compared. ASTM Type HA threads correspond to the standard for bone screws having a spherical undersurface head, a shallow asymmetrical buttress thread, and a deep screw head. ASTM Type HB threads correspond to the standard for bone screws having a spherical undersurface head, a deep asymmetrical buttress thread, and a shallow screw head. ASTM Type HC threads correspond to the standard for bone screws having a conical undersurface head and a symmetrical thread. ASTM Type HD threads correspond to the standard for bone screws having a conical undersurface head and an asymmetrical thread. Column B is the maximum major diameter for the thread including permitted manufacturing tolerances. Column C is the minimum major diameter for the thread including permitted manufacturing tolerances. Column D is the maximum minor diameter for the thread including permitted manufacturing tolerances. Column E is the minimum minor diameter for the thread including permitted manufacturing tolerances. Column F is the thread pitch. Column B/E is the ratio of the maximum major diameter to the minimum minor diameter and represents the largest major diameter to minor diameter ratio for the thread. Column C/D is the ratio of the minimum major diameter to the maximum minor diameter and represents the smallest major diameter to minor diameter ratio for the thread. Column B/F is the ratio of the maximum major diameter to the pitch and represents the largest major diameter to pitch ratio for the thread. Column C/F is the ratio of the minimum major diameter to the pitch and represents the smallest major diameter to pitch ratio for the thread. Column D/F is the ratio of the maximum minor diameter to pitch and represents the largest minor diameter to pitch ratio for the thread. Column E/F is the ratio of the minimum minor diameter to pitch and represents the smallest minor diameter to pitch ratio for the thread.

Referring to columns B/E and C/D, standard bone screws with a thread major diameter less than 4.0 mm have a major diameter to minor diameter ratio less than 1.7.

Referring to column F of Table 3, standard bone screws with a thread major diameter less than 6.5 mm have a pitch less than 2.2 mm. Standard bone screws with a thread major diameter less than 4.5 mm have a pitch equal to or less than 1.75 mm. Standard bone screws with a thread major diameter less than 4.0 mm have a pitch less than 1.5 mm. Looking at it another way, referring to columns B/F and C/F, standard bone screws have a major diameter to pitch ratio greater than 2. Standard bone screws with a thread major diameter less than 4.0 mm have a major diameter to pitch ratio greater than 2.5. Referring to columns D/F and E/F, standard bone screws have a minor diameter to pitch ratio greater than or equal to 1. Standard bone screws with a thread major diameter less than 4.0 mm have a minor diameter to pitch ratio greater than or equal to 1.75.

Examples of the invention have a thread with a smaller minor diameter and/or a larger pitch than standard bone screws of a similar size to, for example, enable the screw thread to bend to follow a curved path in a bone.

Referring to Example 1 according to the invention, the example thread has a 3.5 mm nominal major diameter, a 2.00 mm nominal minor diameter, a pitch of 2.75 mm, a major diameter to minor diameter ratio between 1.68 and 1.82, a major diameter to pitch ratio between 1.25 and 1.29, and a minor diameter to pitch ratio between 0.71 and 0.75. Comparing Example 1 to ASTM HA 3.5 and ASTM HC 3.5, it is seen that the thread of Example 1 has a minor diameter approximately 15-20% smaller than similar sized standard bone screws. In addition, the thread of Example 1 has a pitch more than double the length of similar sized standard bone screws. The major diameter to minor diameter ratio for the thread of Example 1 is approximately 20-30% greater than for similar sized bone screws. The major diameter to pitch ratio for the thread of Example 1 is less than 50% that of similarly sized standard screws and the minor diameter to pitch ratio for the thread of Example 1 is less than 40% that of similarly sized standard bone screws. With its unconventional decreased minor diameter and increased thread pitch, a thread according to Example 1 made of Ti-6Al-4V has been shown by the present inventors to be able to bend to follow the natural curve of the intramedullary canal of a human fibula.

Referring to Example 2 according to the invention, the example thread has a 3.18 mm nominal major diameter, a 1.43 mm nominal minor diameter, a pitch of 2.25 mm, a major diameter to minor diameter ratio between 2.07 and 2.41, a major diameter to pitch ratio between 1.38 and 1.44, and a minor diameter to pitch ratio between 0.60 and 0.67. Comparing example 2 to ASTM HA 3.5 and ASTM HC 2.9, the most similar sized standard bone screw threads, it is seen that the thread of Example 2 has a minor diameter approximately 30-40% smaller than similar sized standard bone screws. In fact, the thread of Example 2 has a minor diameter smaller than an ASTM HA 2.7 thread and most closely resembles that of the much smaller ASTM HA 2.0 thread. In addition, the thread of Example 2 has a pitch more than double that of similar sized standard bone screws. The major diameter to minor diameter ratio for the thread of Example 2 is approximately 50-65% greater than for similar sized bone screws. The major diameter to pitch ratio for the thread of Example 2 is approximately 50% that of similarly sized standard screws and the minor diameter to pitch ratio for the thread of Example 2 is less than 35% that of similarly sized standard bone screws. With its unconventional decreased minor diameter and increased thread pitch, a thread according to Example 2 made of polyetheretherketone has been shown by the present inventors to be able to bend to follow the natural curve of the intramedullary canal of a human clavicle.

Referring to Example 3 according to the invention, the example thread has a 5.18 mm nominal major diameter, a 2.93 mm nominal minor diameter, a pitch of 2.75 mm, a major diameter to minor diameter ratio between 1.70 and 1.84, a major diameter to pitch ratio between 1.85 and 1.91, and a minor diameter to pitch ratio between 1.04 and 1.09. Comparing example 3 to ASTM HA 5.0, the most similar sized standard bone screw thread, it is seen that the thread of Example 3 has a minor diameter approximately 15% smaller than similar sized standard bone screws. In addition, the thread of Example 3 has a pitch approximately 60% greater than similar sized standard bone screws. The major diameter to minor diameter ratio for the thread of Example 3 is approximately 23% greater than for similar sized bone screws. The major diameter to pitch ratio for the thread of Example 3 is approximately 67% that of similarly sized standard screws and the minor diameter to pitch ratio for the thread of Example 3 is less than 55% that of similarly sized standard bone screws. With its unconventional decreased minor diameter and increased thread pitch, a thread according to Example 3 made of polyetheretherketone has been shown by the present inventors to be able to bend to follow the natural curve of the intramedullary canal of a human clavicle.

Examples of threads according to the invention preferably have a pitch greater than that for standard bone screws of a similar major diameter. For example, for threads with a major diameter less than 6.25 mm, it is preferable to have a pitch greater than 2.2 mm; more preferably greater than 2.5; more preferably greater than or equal to 2.75. For threads with a major diameter less than 4.0 mm, it is preferable to have a pitch greater than 1.5 mm; more preferably greater than 1.75; more preferably greater than 2.0; more preferably greater than 2.25; more preferably greater than or equal to 2.75.

Examples of threads according to the invention having a major diameter less than 4.0 mm preferably have a major diameter to minor diameter ratio greater than 1.7; more preferably greater than 1.8; more preferably greater than 1.9; more preferably greater than 2.0.

Examples of threads according to the invention preferably have a major diameter to pitch ratio less than 2; more preferably less than 1.75; more preferably less than 1.5; more preferably less than 1.4; more preferably less than 1.3. For threads having a major diameter less than 4.0 mm, the major diameter to pitch ratio is preferably less than 2.7; more preferably less than 2.5; more preferably less than 2.25.

Examples of threads according to the invention preferably have a minor diameter to pitch ratio less than 1.2; more preferably less than 1.0; more preferably less than 0.8; more preferably less than or equal to 0.75, more preferably less than 0.7.

Figures 8, 9, 10:
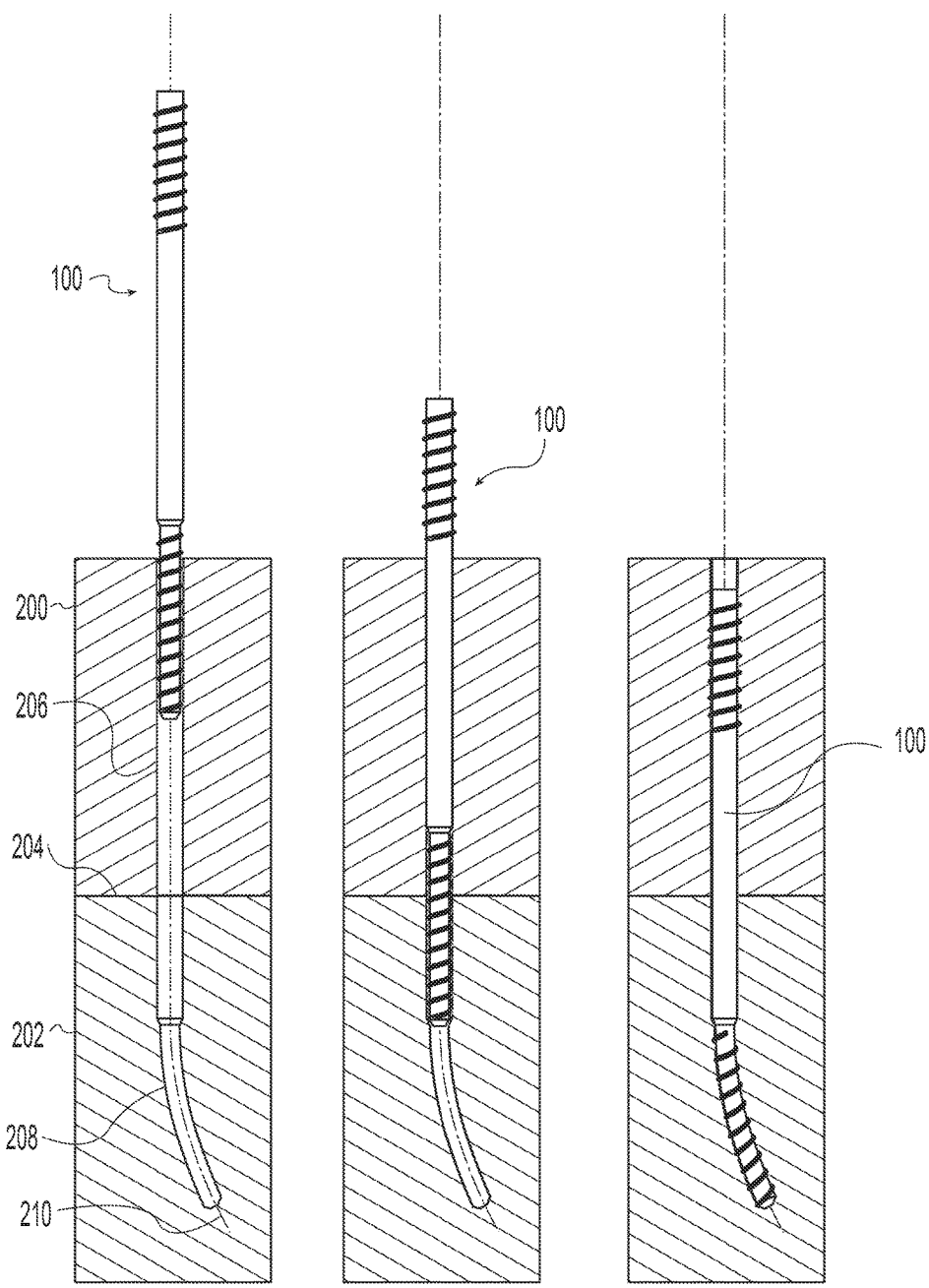
FIGS. 8-10 are partial sectional views showing the insertion of the bone implant of FIG. 1 into bone.

FIGS. 8-10 illustrate an implant being inserted into first and second bone portions 200, 202 having a bone interface 204 between them. The implant could be any of the examples of FIGS. 1, 36, 42, 44, 46 and 50 and the variations described herein. In the particular example of FIGS. 8-10, the example of FIG. 1 is shown. A first or proximal bore 206 is formed in the first bone portion 200, across the bone interface 204, and into the second bone portion 202. A second or distal bore 208 extends distally from the proximal bore 206 defining a curved path 210. The screw 100 is advanced through the proximal bore 206 until the distal screw threads engage the distal bore 208 as shown in FIG. 9. Further advancing the screw 100 causes it to bend to follow the curved path 210 as shown in FIG. 10. Having a straight portion of the path, and thus the straight mid portion of the screw 100, spanning the bone interface results in a zero stress and strain state at the bone interface which prevents separation of the bone portions 200, 202 at the interface 204.

Figure 11:
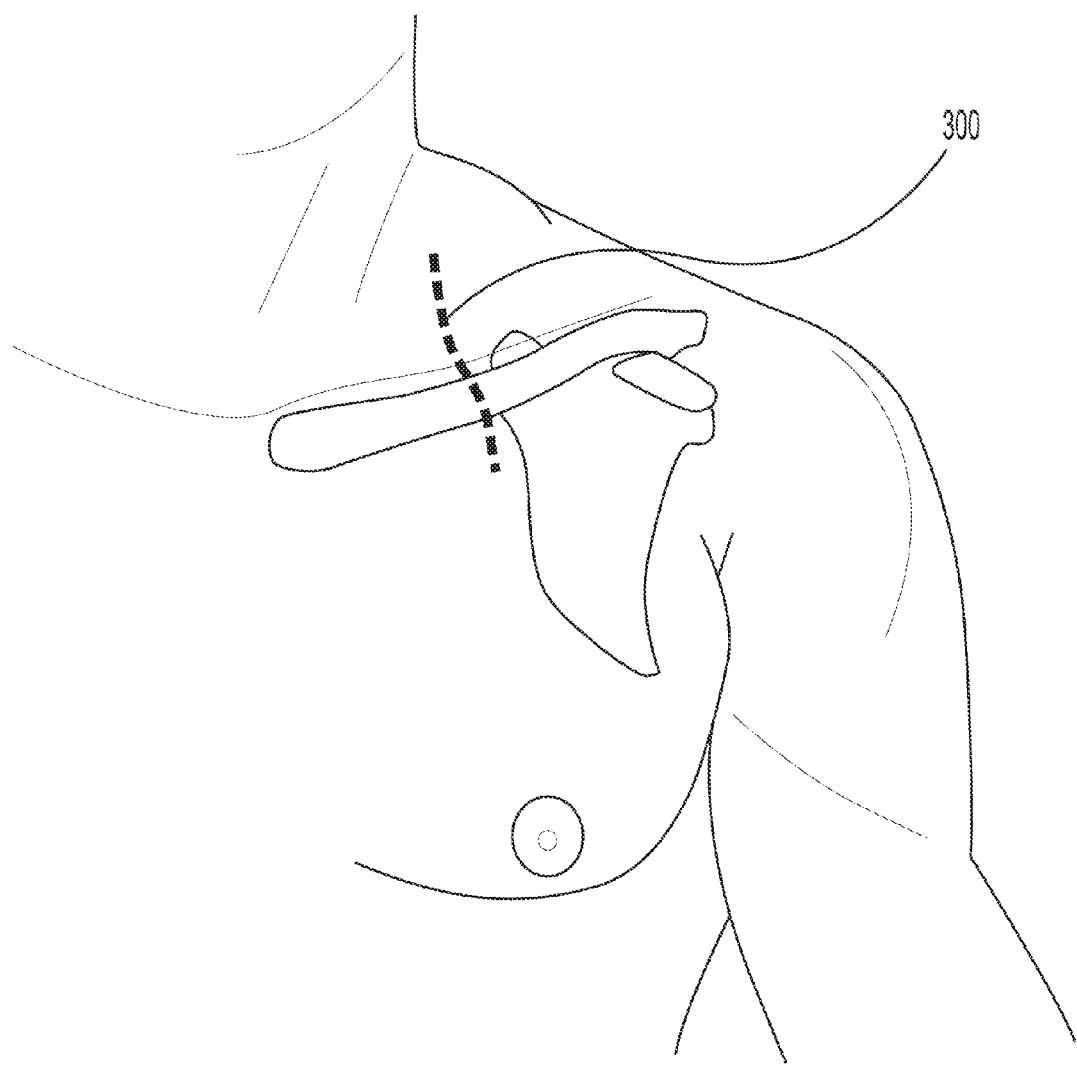
FIGS. 11-35 illustrate a surgical procedure utilizing the bone implant of FIG. 1.

FIGS. 11-35 depict an illustrative method of using an implant to fix a fractured clavicle. The implant could be any of the examples of FIGS. 1, 36, 42, 44, 46 and 50 and the variations described herein. In the particular example of FIGS. 11-35, the example of FIG. 1 is shown. A patient is placed in a beach chair position with the head rotated away from the operative side. A bolster is placed between the shoulder blades and head allowing the injured shoulder girdle to retract posteriorly. A C-arm is positioned to enable anterior-posterior (AP) and cephalic views of the operative site. A 2-3 cm incision 300 is made at the fracture site along Langer's Lines running perpendicular to the long axis of the clavicle to expose the fracture site (FIG. 11). The platysma muscle is freed from the skin and split between its fibers. The middle branch of the supraclavicular nerve is identified and retracted.

Figure 12:
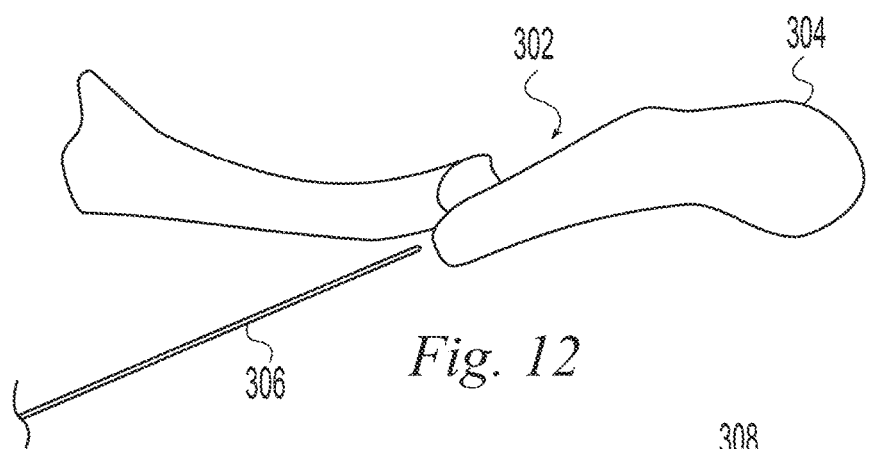

The medial end 302 of the lateral fragment 304 of the fractured clavicle is elevated from the fracture site incision (FIG. 12).

Figure 13:
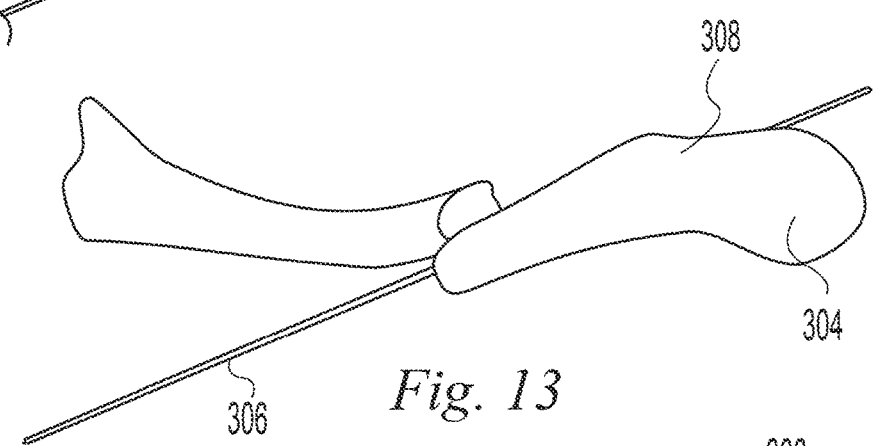

A K-wire 306, e.g. a 1.4 mm K-wire, is drilled into the canal of the lateral fragment 304 and advanced through the dorsolateral cortex 308 and out through the skin (FIG. 13).

Figure 14:
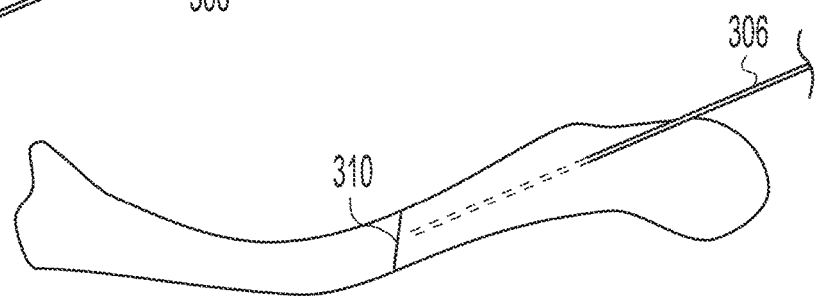

A wire driver is attached to the lateral portion of the K-wire and used to back the wire out until it is lateral to the fracture 310 (FIG. 14). Bone clamps are used at the incision site to reduce the fracture and clamp the bone fragments in position. Proper reduction is confirmed with AP and cephalic radiographic views.

Figure 15:
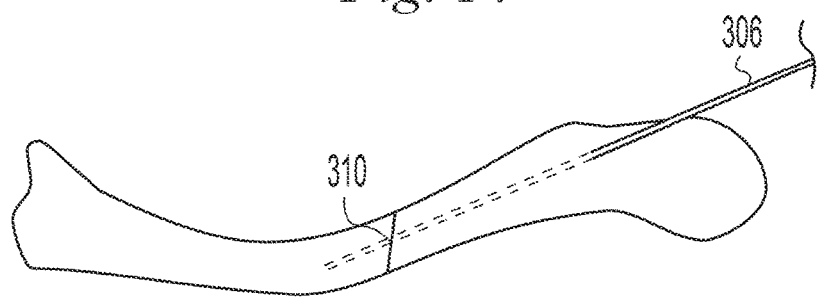

The K-wire 306 is advanced until it is preferably at least 20 mm medial to the fracture (FIG. 15).

Figure 16:
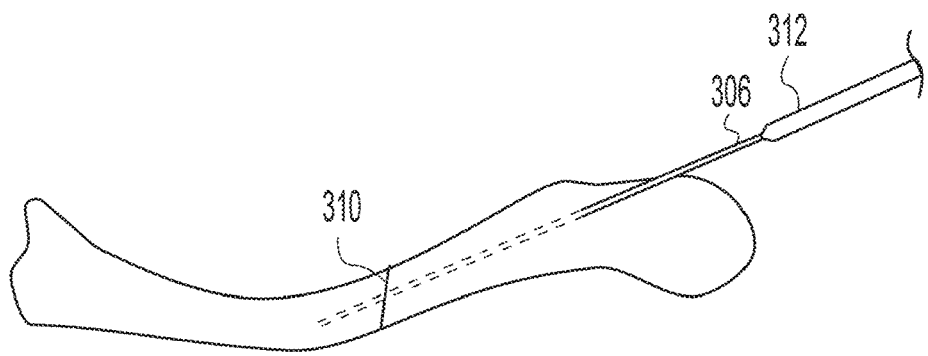
Figure 17:
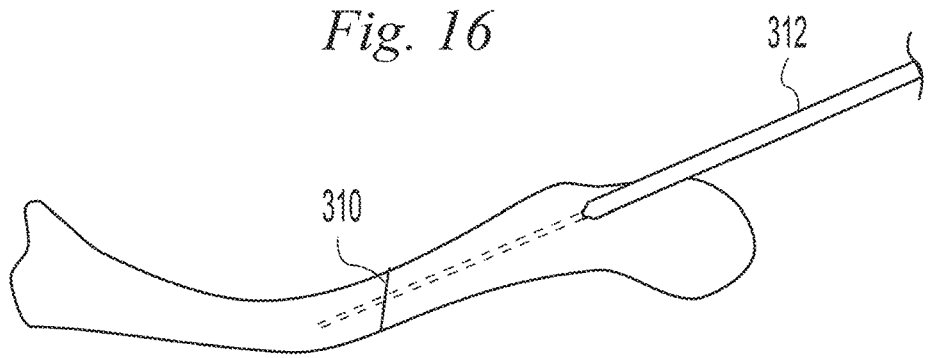

A first dilator 312, e.g. a 3.2 mm dilator, is placed over the K-wire and advanced until it contacts the bone (FIGS. 16-17).

Figure 18:
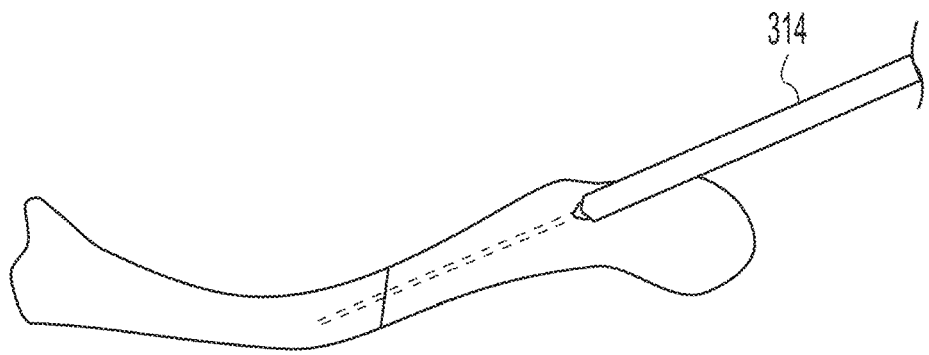

A second dilator 314, e.g. a 4.5 mm dilator, is placed over the first dilator 312 and advanced until it contacts the bone (FIG. 18).

Figure 19:
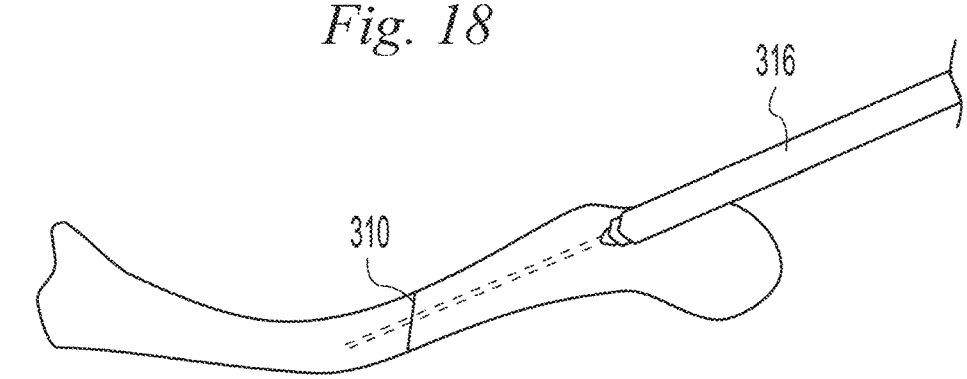

A drill guide 316 is placed over the second dilator 314 and advanced until it contacts the bone (FIG. 19).

Figure 20:
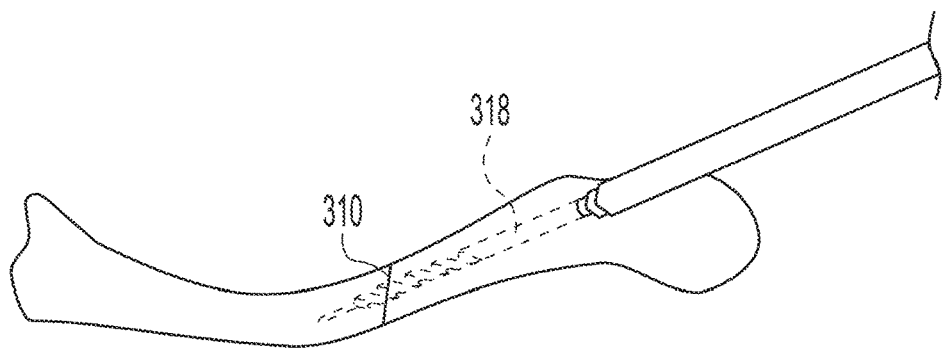

The first dilator 312 is removed and a first lateral drill 318, corresponding to the minor diameter of the distal screw threads, e.g. a 3.2 mm drill, is advanced over the K-wire into the bone, preferably at least 20 mm medial to the fracture. A drill depth mark readable adjacent the drill guide may be noted as a reference for implant sizing (FIG. 20).

Figure 21:
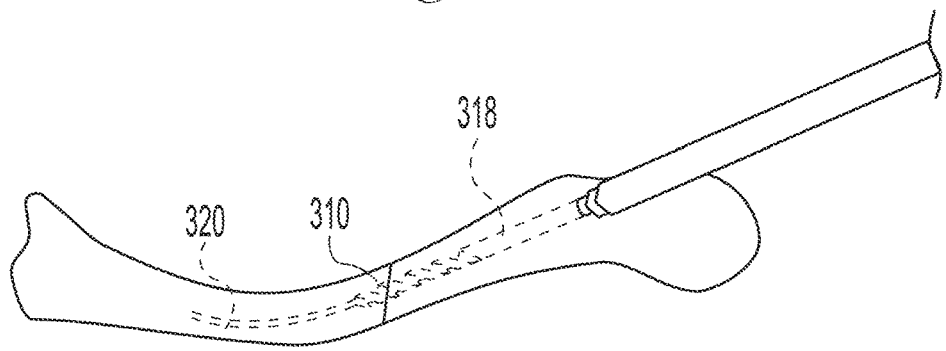
Figure 22:
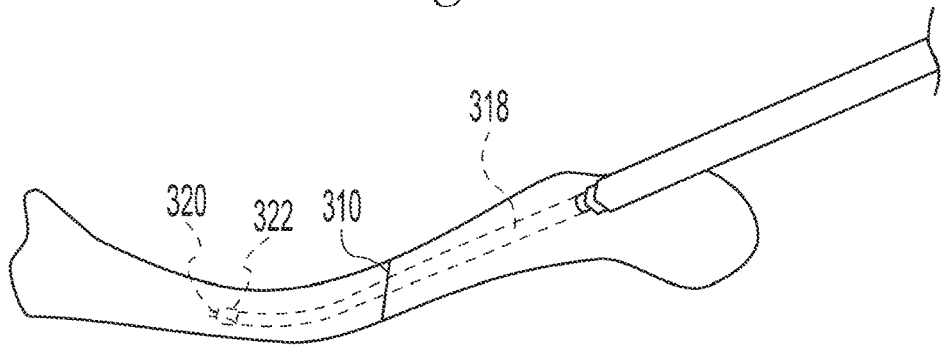

The K-wire is removed and replaced with a flexible guide wire 320, e.g. a nitinol guide wire, sized to fit within the screw cannulation, e.g. a 1.4 mm guide wire. The flexible guide wire 320 is advanced through the first lateral drill and further along the intramedullary canal of the medial bone fragment and will curve to follow the intramedullary canal to define a curved path in the bone. Preferably, the guide wire is advanced approximately 30 mm medial to the tip of the first lateral drill 318 (FIG. 21).

The first lateral drill 318 is removed and a flexible shaft reamer 322, corresponding to the minor diameter of the distal screw threads, is guided over the flexible guide wire 320 to ream the medial portion of the curved path (FIG. 22) The flexible reamer 322 and second dilator 314 are then removed.

Figure 23:
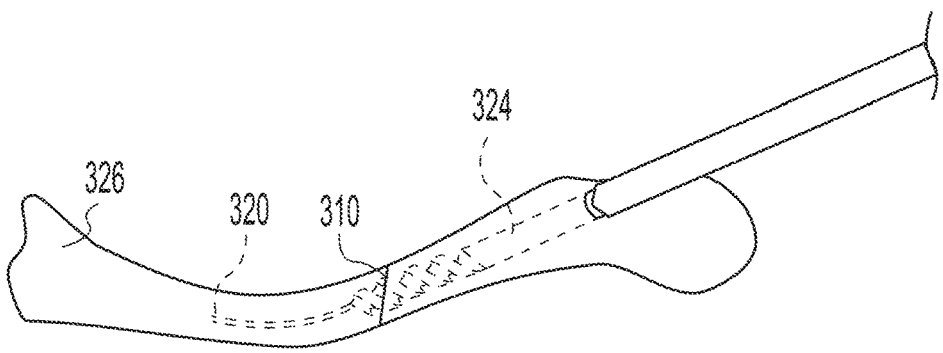

A second lateral drill 324, having a diameter corresponding to the diameter of the mid-portion of the screw, e.g. a 4.5 mm drill, is guided over the flexible guide wire to enlarge the bone hole laterally to receive the mid-portion and proximal portion of the screw 100. The second lateral drill 324 is advanced the same distance as the first lateral drill (FIG. 23). The drilling step may be monitored in A/P and cephalic views with the C-arm to avoid perforating the bone cortex as the second lateral drill 324 is advanced into the medial bone fragment 326.

Figure 24:
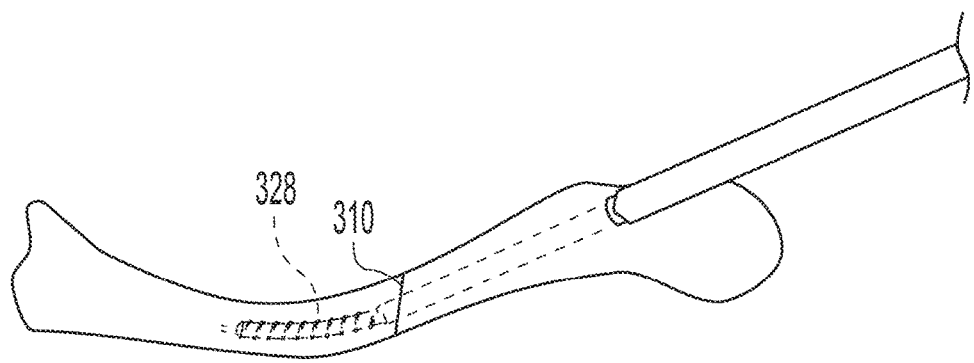

A flexible tap 328, having cutting threads corresponding to the distal threads of the screw 100 is guided over the flexible guide wire to cut threads into the medial bone fragment along the curved path (FIG. 24). The tap may serve as a trial implant and provides tactile feedback regarding the fit of the implant in the bone. If it is determined that a larger screw is desirable, subsequent larger second drills may be used to re-drill the lateral straight portion and subsequent larger flexible taps may be used to increase the distal thread major diameter without having to re-ream the medial curved portion of the bone hole. Once a desired level of thread purchase and canal filling are achieved, a depth mark readable adjacent the drill guide may be noted as a reference for the required implant length. If a screw 100 with a proximal threaded portion is used, a lateral tap may be used to tap the lateral bone fragment to receive the proximal threads.

Figure 25:
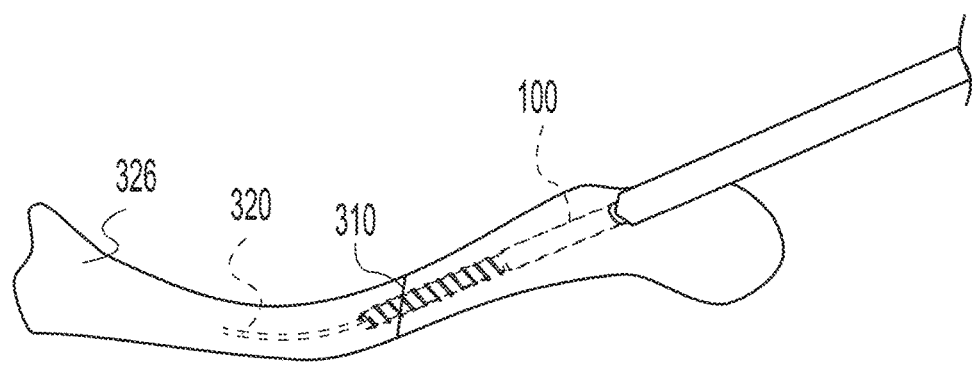
Figure 26:
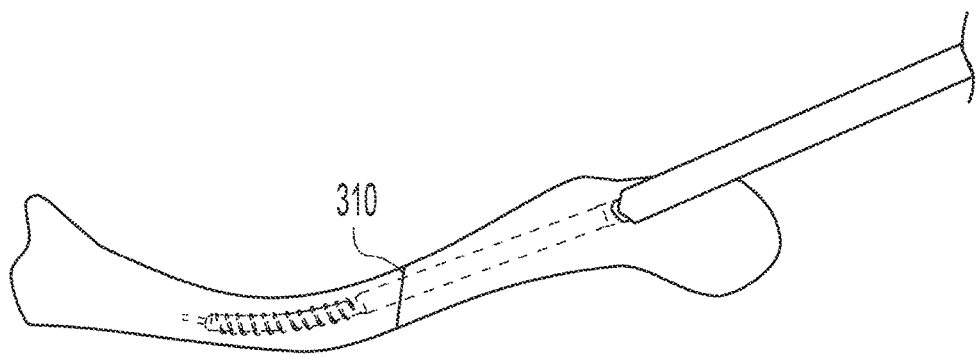

The screw 100 is attached to an inserter 330 and guided over the flexible guide wire until it is fully seated in the prepared threads in the medial bone fragment (FIGS. 25 and 26). Optionally, the screw 100 may be axially driven with a mallet through the lateral bone fragment until just short of the distal thread engagement. The screw 100 may then be threaded into full engagement with the prepared threads in the medial fragment. Radiographic visualization may be used to ensure that the fracture is fully reduced and anatomically aligned in length and rotation.

Figure 27:
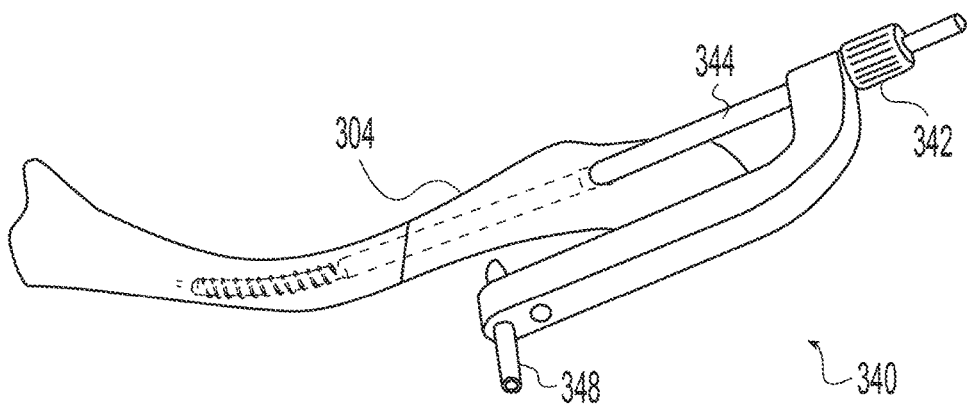

If a proximally threaded screw has not been used, or if additional fixation is otherwise desired, cross fixation may be used. For example, a cross fixation guide 340 may be engaged with the implant inserter 330 (FIG. 27). The cross fixation guide may include a knob 342 that threadingly engages the implant inserter 330 and a cross fixation guide sleeve 344 that abuts the lateral bone fragment adjacent the bone hole entrance. Rotating the knob 342 moves the cross fixation guide sleeve 344 and implant inserter 330 axially relative to one another. With the cross fixation guide sleeve 344 abutting the lateral bone fragment 304, the implant inserter, implant, and medial bone fragment 326 will be drawn laterally and the lateral bone fragment 304 will be pressed medially to apply compression across the fracture.

Figure 28:
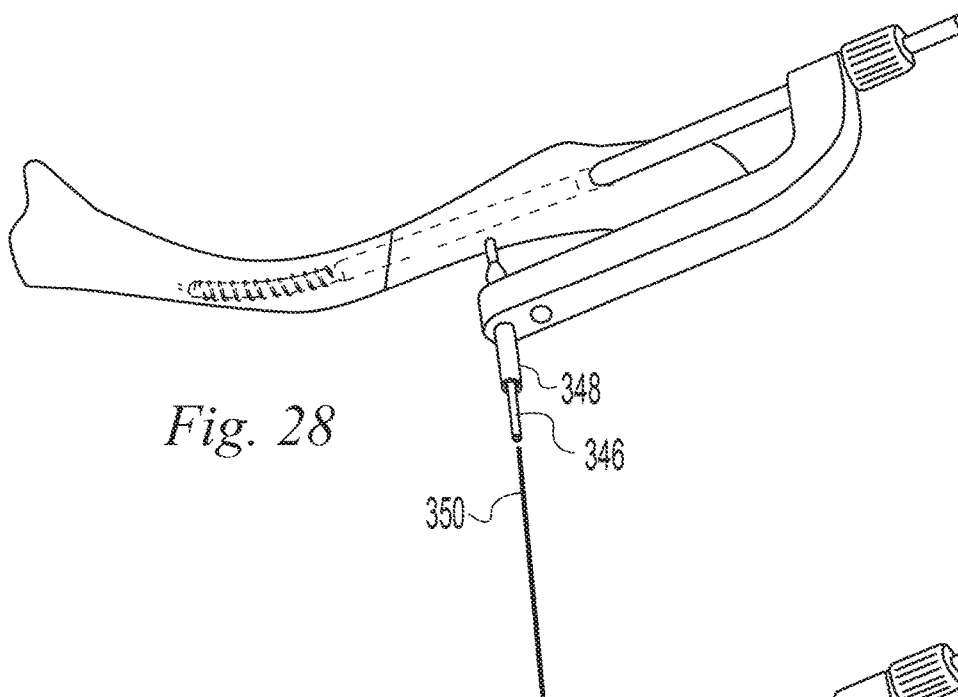

Inner and outer drill sleeves 346, 348 are advanced through the guide 340 until they abut the bone (FIG. 28). In the case of a screw such as the examples of FIGS. 36, 42, 44, 46 and 50 having one or more preformed transverse bores, the cross fixation guide may have one or more targeting holes positioned to align with the one or more transverse bores. In the case of a screw such as the example of FIG. 1 not having preformed transverse bores, cross fixation may be inserted directly through the screw 100 forming a transverse bore intraoperatively.

Figure 29:
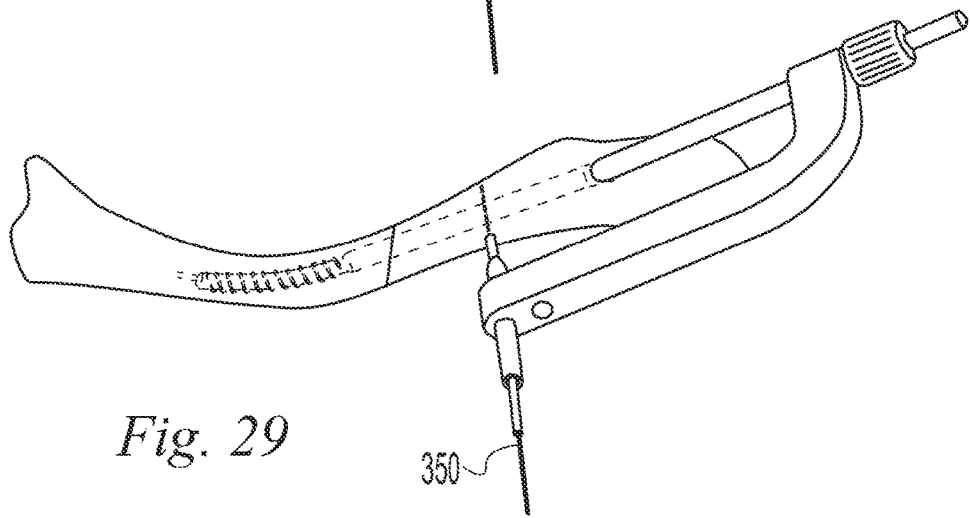

For example, a cross fixation wire 350 may be guided through the drill sleeves, through the near cortex, through the mid or proximal portions of the screw, and into the far cortex of the lateral bone fragment (FIG. 29). If wire cross fixation is adequate, the cross fixation guide may be removed and the wire may be trimmed flush with the bone surface.

Figure 30:
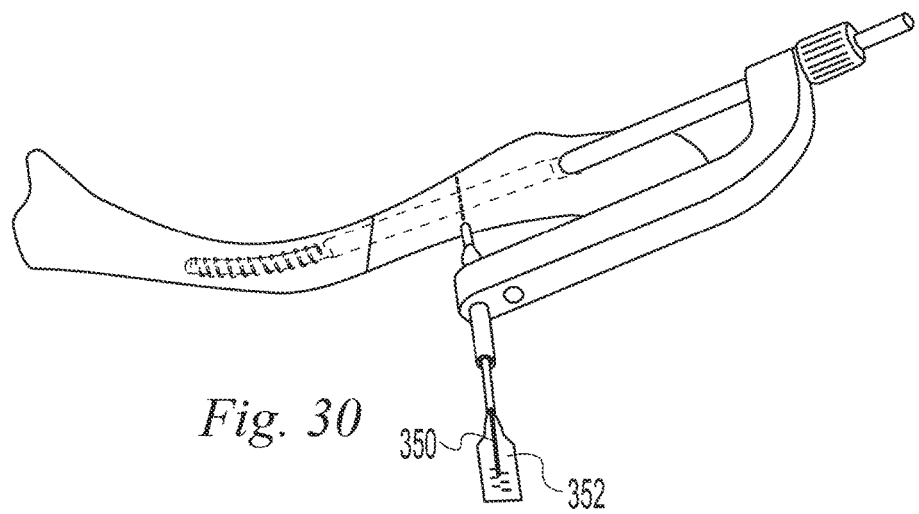

However, if screw cross fixation is desired, a screw depth gauge 352 may be placed over the cross fixation wire to measure the projecting portion of the guide wire to determine the required screw length for bi-cortical fixation (FIG. 30).

Figure 31:
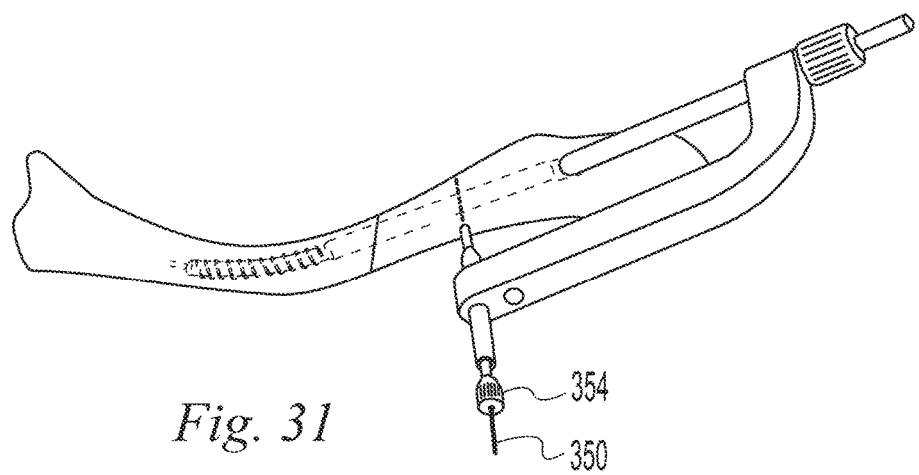

A countersink tool 354 may be used to create a countersink for a cross fixation bone screw 356 (FIG. 31).

Figure 32:
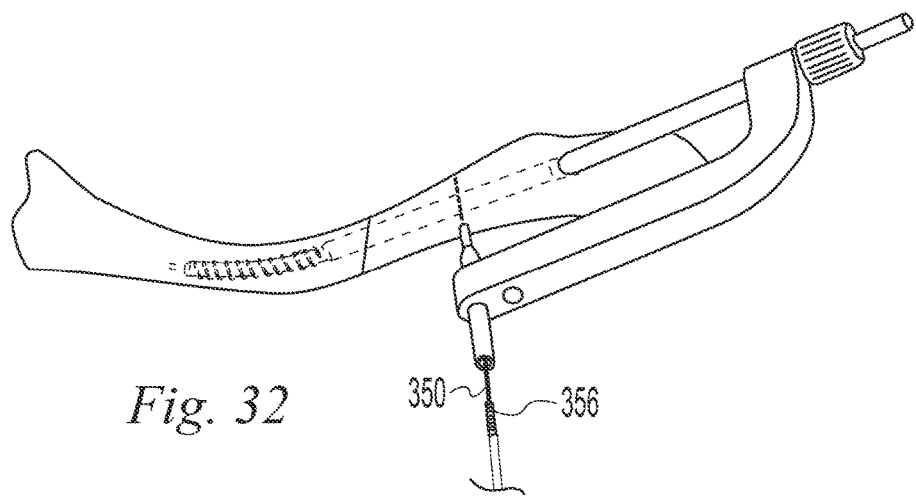

The appropriate length cross fixation screw 356 may then be guided over the cross fixation wire 350 and seated into the bone (FIG. 32). These steps may be repeated to place additional screws if desired.

Figure 33:
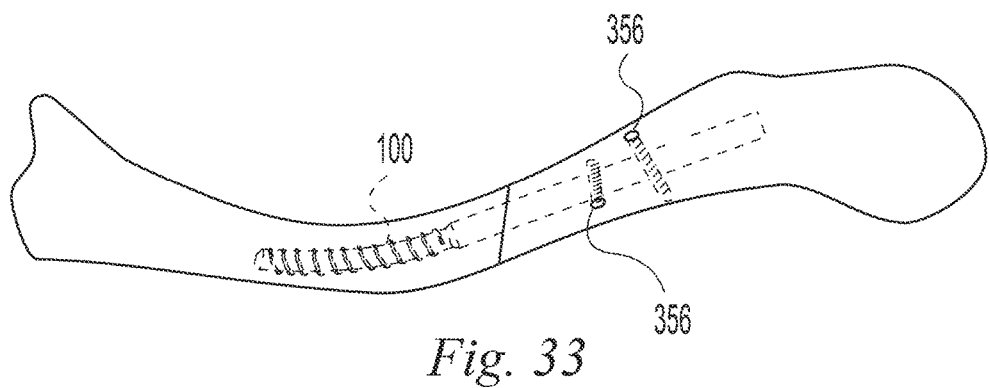
Figure 34:
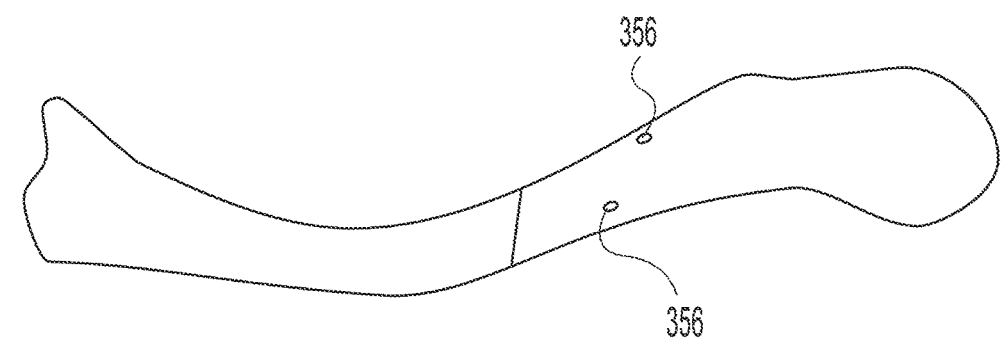

FIGS. 33 and 34 illustrate the location of the screw 100 and cross fixation screws 356 relative to the lateral and medial bone fragments.

Figure 35:
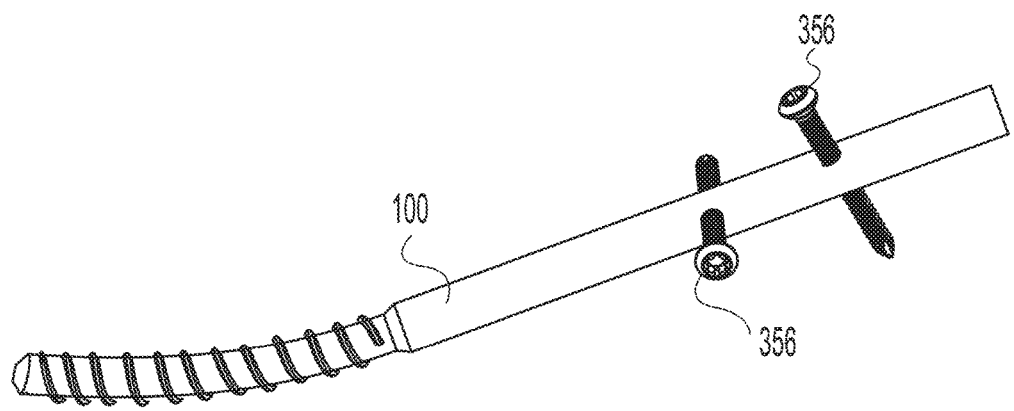

FIG. 35 illustrates the cross fixation screws 356 in the screw 100 without the bone to obscure the view. Preferably the screw 100 is made of a relatively soft material, e.g. a polymer, that facilitates arbitrary placement of the cross fixation screws at any desired location.

Figure 54:
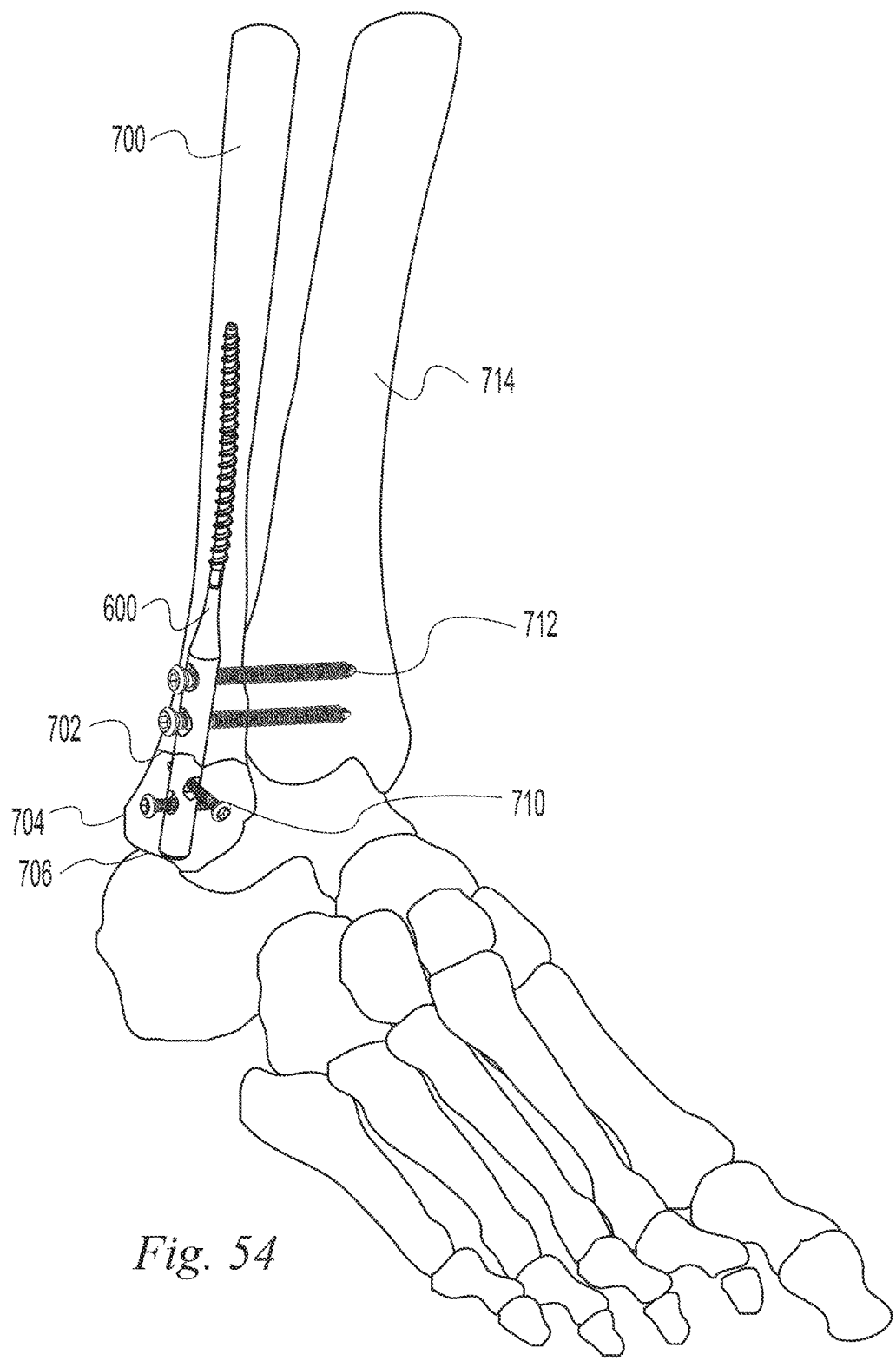
FIG. 54 is a perspective view of a surgical application of a bone implant according to one example of the invention.

FIG. 54 illustrates a repair utilizing an implant according to one example of the invention. In the example of FIG. 54, the implant 600 of FIGS. 50-53 is used to repair a fibula 700 having a distal fracture 702 and fragment 704. The implant 600 is inserted through the distal end 706 of the fragment 704 into the intramedullary canal of the fibula. As the implant is rotated, the distal threaded portion engages the bone and pulls the proximal portion into the bone to a position bridging the fracture 702. The distal threaded portion bends to follow the curved path of the intramedullary canal. Bone screws 710 are placed into the fragment and the first pair of holes 606 of the implant 600 to secure the fragment. Additional screws 712 are placed into the fibula, the second pair of holes 612, and the tibia 714 to reinforce the syndesmosis joint between the fibula and tibia.

Figure 55:
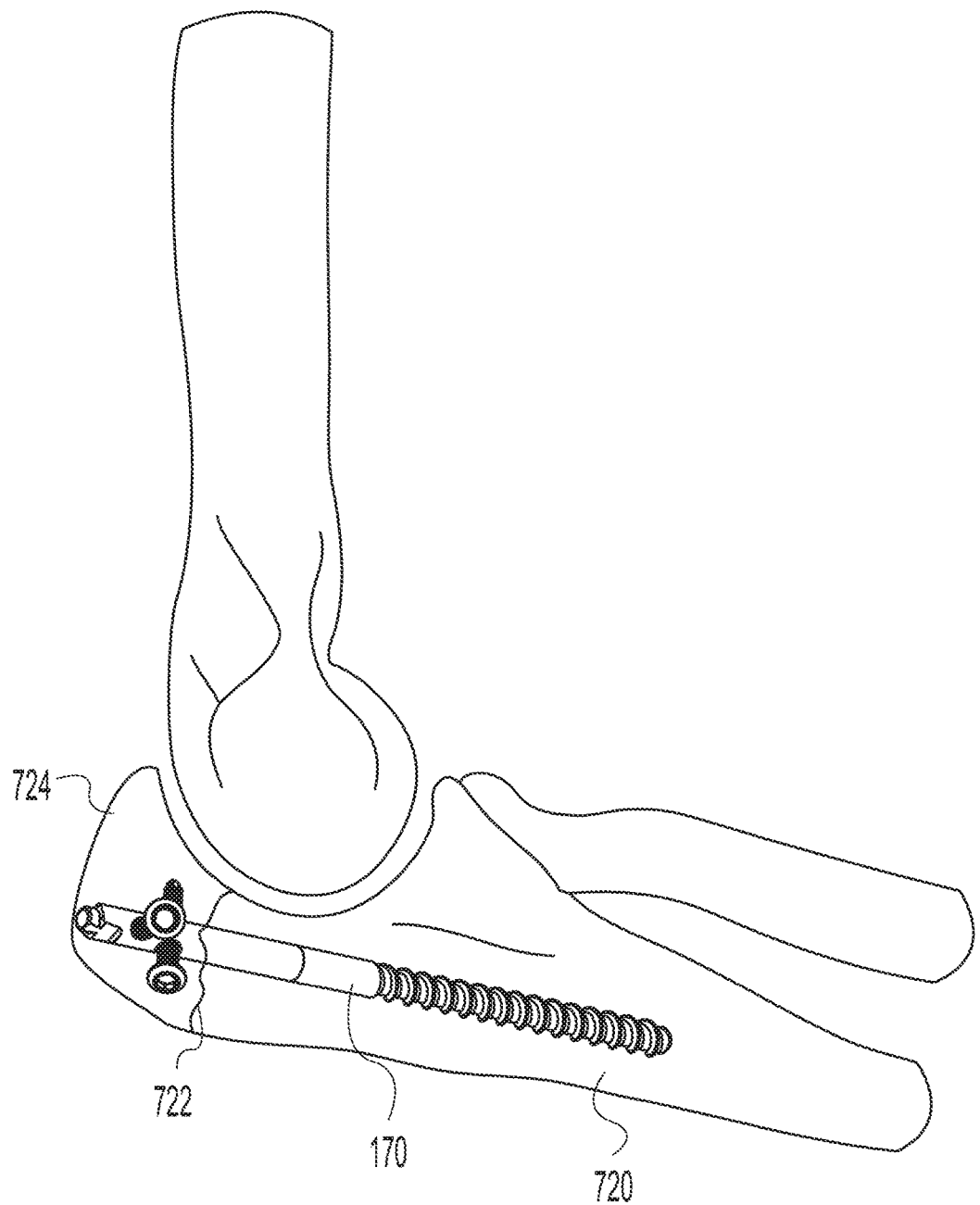
FIG. 55 is a perspective view of a surgical application of a bone implant according to one example of the invention.

FIG. 55 illustrates a repair utilizing an implant according to one example of the invention. In the example of FIG. 54, the implant 170 of FIGS. 36-41 is used to repair an olecranon fracture of an ulna 720 having a fracture 722 and a fragment 724. The implant 170 is inserted through the fragment 724 into the intramedullary canal of the ulna 720. As the implant is rotated, the distal threaded portion engages the bone and pulls the proximal portion into the bone to a position bridging the fracture 722. The distal threaded portion bends to follow the curved path of the intramedullary canal. Bone screws are placed into the fragment and the holes of the implant 170 to secure the fragment.

Figure 56:
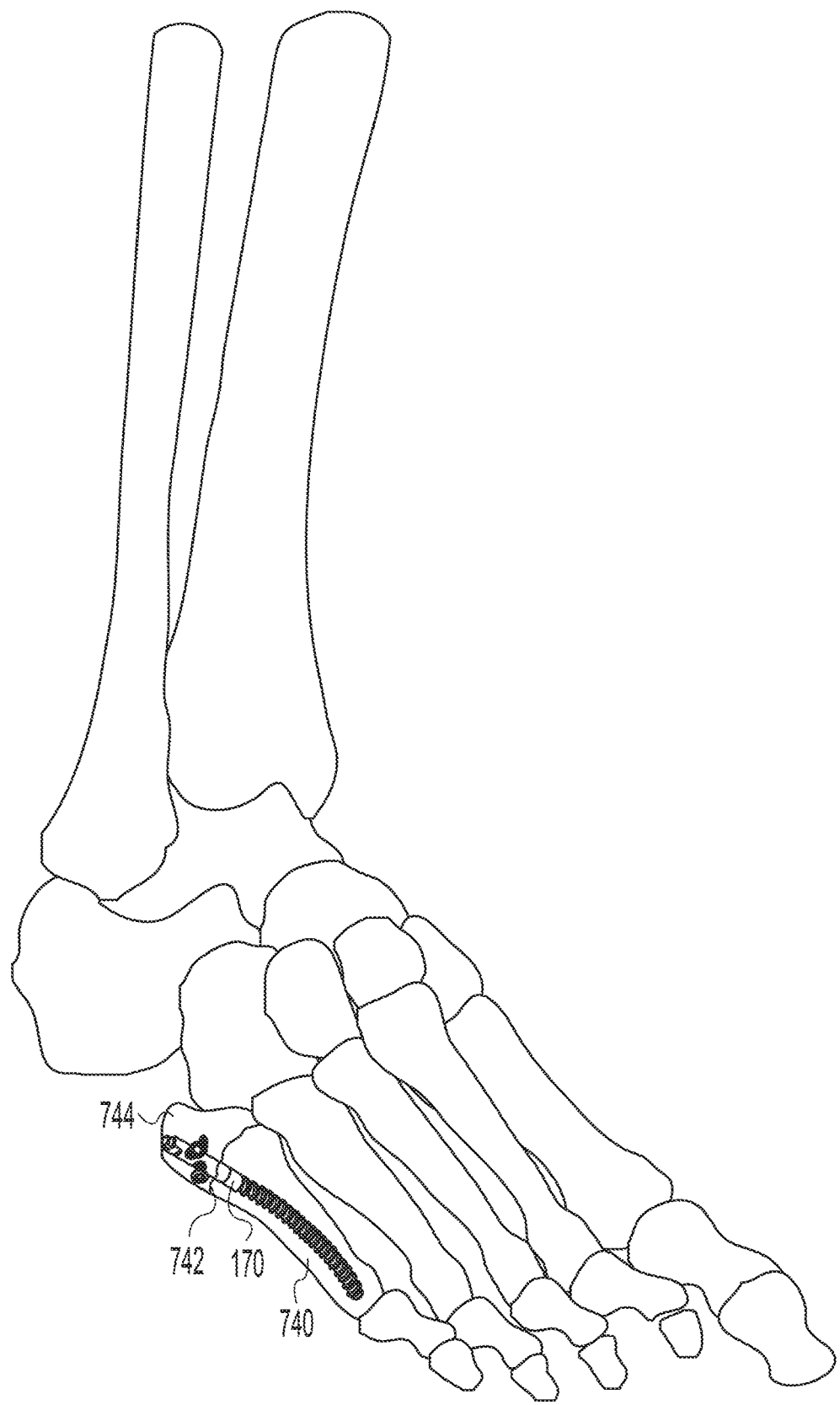
FIG. 56 is a perspective view of a surgical application of a bone implant according to one example of the invention.

FIG. 56 illustrates a repair utilizing an implant according to one example of the invention. In the example of FIG. 55, the implant 170 of FIGS. 36-41 is used to repair a Jone's fracture of a fifth metatarsal 740 having a fracture 742 and a fragment 744. The implant 170 is inserted through the fragment 744 into the intramedullary canal of the ulna 720. As the implant is rotated, the distal threaded portion engages the bone and pulls the proximal portion into the bone to a position bridging the fracture 742. The distal threaded portion bends to follow the curved path of the intramedullary canal. Bone screws are placed into the fragment and the holes of the implant 170 to secure the fragment.

Various examples have been presented to aid in illustrating the invention. These various examples are illustrative but not comprehensive and variations may be made within the scope of the invention. For example, the various features described relative to each example may be interchanged among the examples.

What is claimed is:

1. A bone implant for stabilizing bone fractures, the bone implant comprising:
    a body defining a longitudinal axis extending between a proximal end and a distal end, the body having a mid-portion between the proximal end and the distal end;
    an elongate distal portion of the body having an outer surface defining a distal screw thread, the distal screw thread having a minor diameter, a major diameter, and a pitch, wherein a ratio of the major diameter to the pitch is less than 2.0 and a ratio of the minor diameter to the pitch is less than or equal to 1.2;
    an elongate, headless, proximal portion of the body having a non-threaded outer surface portion having a proximal portion diameter; and
    a mid-portion positioned adjacent to the distal end threads, between the proximal end and the distal end, the mid-portion having a mid-portion diameter that is greater than or equal to the major diameter of the distal screw thread and the proximal portion diameter.

2. The bone implant of claim 1 wherein the major diameter is less than 4.0 mm and a ratio of the major diameter to the minor diameter is greater than 1.7.

3. The bone implant of claim 1 wherein the major diameter is less than 4.0 mm and a ratio of the major diameter to the minor diameter is greater than 2.0.

4. The bone implant of claim 1 wherein a ratio of the major diameter to the pitch is less than 1.5.

5. The bone implant of claim 1 wherein the major diameter is less than 4.0 mm.

6. The bone implant of claim 1 wherein a ratio of the minor diameter to the pitch is less than or equal to 0.75.

7. The bone implant of claim 1 further comprising a passage formed through the elongate, headless proximal portion transverse to the longitudinal axis from a first opening on a surface of the proximal portion to a second opening on the surface of the proximal portion.

8. The bone implant of claim 7 wherein the elongate, headless proximal portion has a length measured from a free end through the mid portion to a proximal start of the distal screw thread, the elongate, headless proximal portion having a maximum diameter, the maximum diameter being uniform over at least one-fourth of the length.

9. The bone implant of claim 8 further comprising a driver engaging feature formed at the proximal end for engaging a driver in torque transmitting relationship, the driver engaging feature having a maximum dimension normal to the longitudinal axis that is less than or equal to the maximum diameter.

10. The bone implant of claim 9 wherein the driver engaging feature is centered on and aligned with the longitudinal axis.

11. The bone implant of claim 1 wherein the body comprises a sleeve surrounding a separate core, the sleeve and core being joined together to form the body.

12. The bone implant of claim 11 wherein the elongate distal portion is operable to bend as it is threaded into a bone to follow a curved path.

13. The bone implant of claim 1 further comprising a helical thread formed on the elongate, headless proximal portion.

14. The bone implant of claim 13 wherein the mid-portion is between the distal screw thread and the helical thread, wherein the helical thread has a helical thread major diameter and a helical thread minor diameter, the helical thread minor diameter being equal to the diameter of the mid-portion.

15. A bone implant for stabilizing bone fractures, the bone implant comprising:
    a body defining a longitudinal axis extending between a proximal end and a distal end;
    an elongate distal portion of the body having an outer surface defining a distal screw thread, the distal screw thread having a minor diameter, a major diameter, and a pitch;
    an elongate, headless, proximal portion of the body having a non-threaded outer surface having a diameter, the diameter of the elongate, headless, proximal portion being greater than or equal to the major diameter of the distal screw thread; and
    a passage formed through the elongate, headless proximal portion transverse to the longitudinal axis from a first opening on a surface of the proximal portion to a second opening on the surface of the proximal portion;
    wherein a ratio of the major diameter to the pitch is sufficiently low to allow the elongate distal portion to be operable to bend as it is threaded into a bone to follow a curved path, wherein:
    the major diameter is less than 4.0 mm;
    the ratio of the major diameter to the minor diameter is greater than 1.7; and
    a ratio of the minor diameter to the pitch is less than 1.0.

16. The bone implant of claim 15, wherein:
    the elongate, headless proximal portion has a length measured from a free end to a proximal start of the distal screw thread, the elongate, headless proximal portion having a maximum diameter, the maximum diameter being uniform over at least one-fourth of the length; and
    the bone implant further comprises a driver engaging feature formed at the proximal end for engaging a driver in torque transmitting relationship, the driver engaging feature having a maximum dimension normal to the longitudinal axis that is less than or equal to the maximum diameter.

17. The bone implant of claim 15, wherein:
    the body comprises a sleeve surrounding a separate core, the sleeve and core being joined together to form the body.

18. A bone implant for stabilizing bone fractures, the bone implant comprising:
    a body defining a longitudinal axis extending between a proximal end and a distal end;
    an elongate distal portion of the body having an outer surface defining a distal screw thread, the distal screw thread having a minor diameter, a major diameter, and a pitch;
    an elongate, headless, proximal portion of the body having a non-threaded outer surface having a diameter, the diameter of the elongate, headless, proximal portion being greater than or equal to the major diameter of the distal screw thread;

a passage formed through the elongate, headless proximal portion transverse to the longitudinal axis from a first opening on a surface of the proximal portion to a second opening on the surface of the proximal portion; and wherein:
the major diameter is less than 6.5 mm;
the pitch is greater than 2.2 mm;
the elongate, headless proximal portion has a length measured from a free end to a proximal start of the distal screw thread, the elongate, headless proximal portion having a maximum diameter, the maximum diameter being uniform over at least one-fourth of the length;
the body comprises a sleeve surrounding a separate core, the sleeve and core being joined together to form the body;
the elongate distal portion is operable to bend as it is threaded into a bone to follow a curved path; and
the bone implant further comprises a driver engaging feature formed at the proximal end for engaging a driver in torque transmitting relationship, the driver engaging feature having a maximum dimension normal to the longitudinal axis that is less than or equal to the maximum diameter.

19. A bone implant for stabilizing bone fractures, the bone implant comprising:
a body defining a longitudinal axis extending between a proximal end and a distal end, the proximal end having a driver engagement feature, centered on and aligned with the longitudinal axis, for engaging a driver in a torque transmitting relationship;
an elongate distal portion of the body having an outer surface defining a distal screw thread, the distal screw thread having a minor diameter, a major diameter, and a pitch; and
an elongate, headless, proximal portion of the body having a non-threaded outer surface having a diameter, the diameter of the elongate, headless, proximal portion being greater than or equal to the major diameter of the distal screw thread;
wherein:
the body comprises a sleeve, with a first modulus of elasticity, surrounding a core, with a second modulus of elasticity;
the elongate distal portion is operable to bend as it is threaded into a bone to follow a curved path; and
the second modulus of elasticity is greater than the first modulus of elasticity.

20. A bone implant for stabilizing bone fractures, the bone implant comprising:
a body defining a longitudinal axis extending between a proximal end and a distal end;
an elongate distal portion of the body having an outer surface defining a continuous distal screw thread, the distal screw thread having a continuous minor diameter, a major diameter, and a pitch; and
an elongate, headless, proximal portion of the body having a smooth outer surface having a diameter, the diameter of the elongate, headless, proximal portion being greater than or equal to the major diameter of the distal screw thread, the proximal portion having a driver engagement feature centered on and aligned with the longitudinal axis;
wherein the elongate distal portion is operable to bend as it is threaded into a bone to follow a curved path.

21. A bone implant for stabilizing bone fractures, the bone implant comprising:
a body defining a longitudinal axis extending between a proximal end and a distal end;
an elongate distal portion of the body having an outer surface defining a distal screw thread, the distal screw thread having a minor diameter, a major diameter, and a pitch;
an elongate, headless, proximal portion of the body having a non-threaded outer surface having a diameter, the diameter of the elongate, headless, proximal portion being greater than or equal to the major diameter of the distal screw thread;
a passage formed through the elongate, headless proximal portion transverse to the longitudinal axis from a first opening on a surface of the proximal portion to a second opening on the surface of the proximal portion; and wherein:
the major diameter is less than 4.0 mm;
the pitch is greater than 1.5 mm;
the elongate, headless proximal portion has a length measured from a free end to a proximal start of the distal screw thread, the elongate, headless proximal portion having a maximum diameter, the maximum diameter being uniform over at least one-fourth of the length;
the body comprises a sleeve surrounding a separate core, the sleeve and core being joined together to form the body;
the elongate distal portion is operable to bend as it is threaded into a bone to follow a curved path; and
the bone implant further comprises a driver engaging feature formed at the proximal end for engaging a driver in torque transmitting relationship, the driver engaging feature having a maximum dimension normal to the longitudinal axis that is less than or equal to the maximum diameter.

* * * * *